(12) United States Patent
Schmeer et al.

(10) Patent No.: US 6,365,393 B1
(45) Date of Patent: Apr. 2, 2002

(54) PARAPOXVIRUSES CONTAINING FOREIGN DNA, THEIR PRODUCTION AND THEIR USE IN VACCINES

(75) Inventors: Norbert Schmeer, Haan; Walter Strube, Pulheim; Mathias Büttner, Tübingen; Hans-Joachim Rziha, Köln, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/125,642

(22) PCT Filed: Feb. 17, 1997

(86) PCT No.: PCT/EP97/00729

§ 371 Date: Aug. 20, 1998

§ 102(e) Date: Aug. 20, 1998

(87) PCT Pub. No.: WO97/32029

PCT Pub. Date: Sep. 4, 1997

(30) Foreign Application Priority Data

Feb. 28, 1996 (DE) .......................... 196 07 458
Sep. 26, 1996 (DE) .......................... 196 39 601

(51) Int. Cl.[7] ........................... C12N 7/01; C12N 15/863
(52) U.S. Cl. .............................. 435/235.1; 435/320.1; 424/199.1
(58) Field of Search ................... 536/237.2; 424/199.1; 435/235.1, 320.1, 69.1, 69.3, 5, 6

(56) References Cited

U.S. PATENT DOCUMENTS 5,766,882 A * 6/1998 Falkner et al. ............. 435/69.1

OTHER PUBLICATIONS

Robinson et al. Virology 157:13–23, 1987.*
Lyttle et al. Journal of Virology 68:84–92, Jan. 1994.*
Mercer et al. Virology 157:1–12, 1987.*
Naase et al. Journal of GeneralVirology 72:1177–1181, 1991.*
Robinson et al (In: Revombinant Poxviruses, ed. Binns et al, CRC press, Boca Raton, pp. 285–325, 1992).*
Mayr et al. J Vet Med Ser B 36 (2). 81–99, (Abstract only), 1989.*
Valpotic et al. Veterinarski Arhiv 63(4):p161–172 (Abstract only), 1993.*
Fleming et al. Journal of General Virology 76:2969–2978, 1995.*
Mayr et al. Zentralbl Beterinaermed Reihe B 28 (7). 535–552, 1981.*
Ramshaw et al. Trends in Biotechnology 10:424–6, 1987.*
Leong et al. Journal 68:8125–8130, 1994.*
Fleming et al. Virology 187:464–471, 1992.*

* cited by examiner

*Primary Examiner*—Mary E. Mosher
(74) *Attorney, Agent, or Firm*—Joseph C. Gil; Godfried R. Akorli

(57) ABSTRACT

The present invention relates to recombinantly prepared parapoxviruses which carry, in their genomes, deletions or insertions in the form of foreign hereditary information and contain hereditary information, to the preparation of such constructs and to their use in vaccines.

10 Claims, 8 Drawing Sheets

HIND III RESTRICTION MAP OF ORF VIRUS STRAIN D1701

Map of pORF-1/-2

FIG. 2

HIND III RESTRICTION MAP OF ORF VIRUS STRAIN D1701

FIG. 4
pORF-1
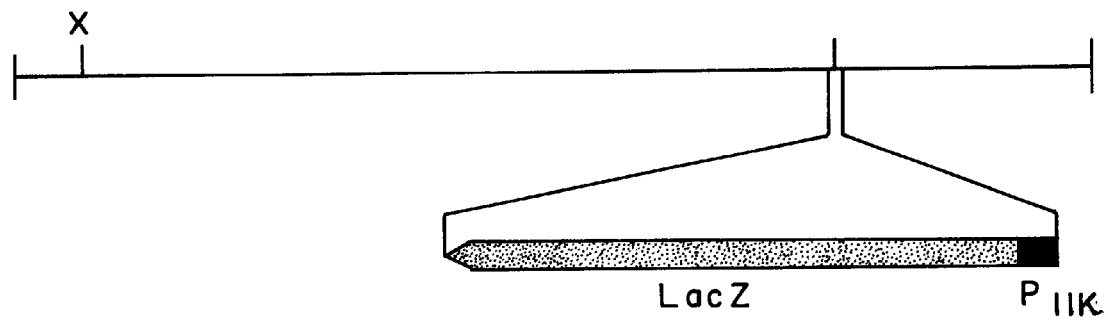
pCE-9

FIG. 5
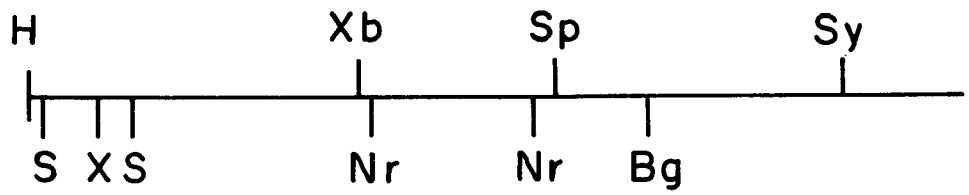
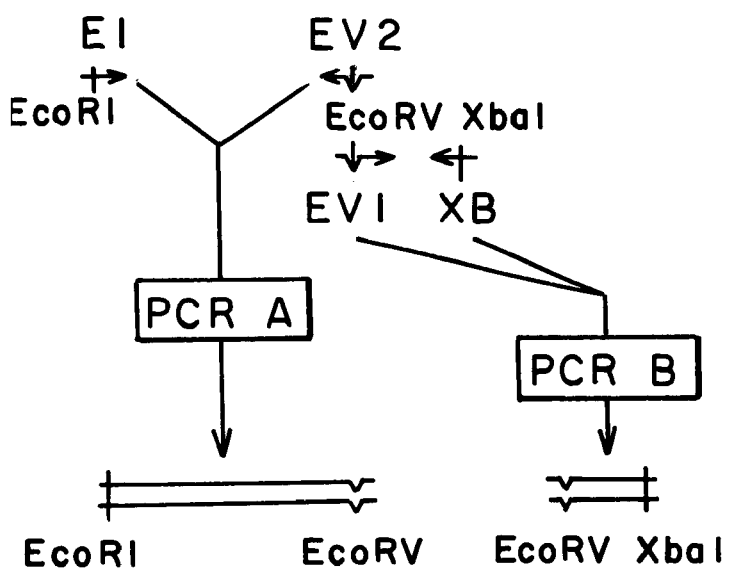
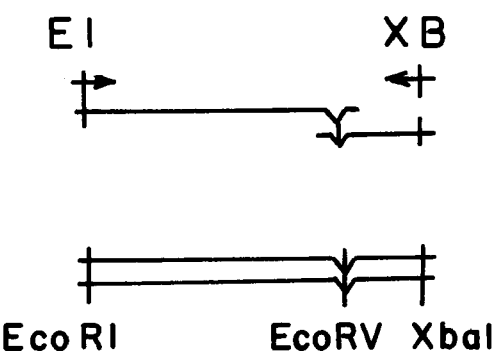

PARAPOXVIRUSES CONTAINING FOREIGN DNA, THEIR PRODUCTION AND THEIR USE IN VACCINES

The present invention relates to recombinant parapoxviruses, to their preparation, and to vaccines and immunomodulators which contain them.

The novel, recombinantly altered parapoxviruses carry deletions and/or insertions in their genome. The deletion of segments of the genome of the parapoxviruses and/or the insertion of foreign DNA can lead to the reduction or loss of their pathogenicity (attenuation). Hereditary information from pathogens or biologically active substances is incorporated into the genome of the parapoxviruses by means of insertions. This foreign hereditary information is, as a constituent of the recombinant parapoxviruses, expressed, for example, in cell cultures, tissues or in intact organisms.

The recombinant parapoxviruses which have been prepared in accordance with the invention are employed, for example, in vaccines or immunomodulators. Expression of the foreign DNA in the genome of the parapoxviruses elicits, for example in a vaccinated individual, a defensive reaction against the pathogens which are represented by the foreign hereditary information. The non-specific resistances of the vaccinated individual can also be stimulated. (In that which follows, the term parapoxviruses is abbreviated to PPV).

PPV can themselves have an immunomodulatory effect since they stimulate non-pathogen-specific immune reactions in the organism. Thus, preparations of parapoxviruses are, for example, successfully employed in veterinary medicine for increasing general resistance.

While vaccines which have a pathogen-specific effect require several days to weeks, depending on the antigen, for establishing protection, they then provide long protection which lasts for months to years.

Consequently, vaccines which are prepared on the basis of recombinant parapoxviruses can be employed as biological products for the improved control of infectious diseases since they build up a long-lasting pathogen-specific immunity in the organism and also induce a non-pathogen-specific protection which sets in very rapidly.

The combination of the immunostimulatory properties of the PPV and the expression of foreign antigens which induce a homologous and/or heterologous pathogen-specific protection is novel. This permits the preparation of products which both mediate a rapid-onset, broad non-pathogen-specific protection against infections and also provide a long-lasting, pathogen-specific protection against infection.

The family of the vertebrate poxviruses (Chordopoxvirinae) is subdivided into individual, independent genera. The present invention relates to the genus of the PPV, which differ both structurally and genetically from the other poxviruses. The PPV are divided into three different species (Lit. #1):

- Parapoxvirus ovis (also termed ecthyma contagiosum virus, contagious pustular dermatitis virus or orf virus), which is regarded as the prototype of the genus,
- Parapoxvirus bovis 1 (also termed bovine papular stomatitis virus or stomatitis papulosa virus) and
- Parapoxvirus bovis 2 (also termed udderpoxvirus, paravaccinia virus, pseudocowpox virus or milker's nodule virus).

Parapoxvirus representatives which have been isolated from camels, red deer, chamois, seals and sealions have also been described. Whether these viruses are autonomous species within the parapoxvirus genus or whether they are isolates of the above-described species has still not been finally clarified.

Infections with PPV can elicit local diseases in both animals and man (zoonotic pathogens). Lit. #1 provides an overview of the syndromes which have so far been described. Prophylactic measures, such as vaccines, can be used to control the diseases. However, the activity of the vaccines which have thus far been obtainable, and which have been developed exclusively on the basis of Parapoxvirus ovis, is unsatisfactory (Lit. #2).

The invention relates to using PPV as a vector for foreign genetic information which is expressed.

Vectors based on avipox, racoonpox, capripox, swinepox or vaccinia virus have already been described as vectors for expressing foreign genetic information. The insights which have been gained in this connection cannot be transferred to PPV. As comparative investigations have demonstrated, there are morphological, structural and genetic differences between the individual genera of the poxviruses. Thus, serological methods can, for example, be used to differentiate the PPV from other poxvirus genera, a fact which is attributable to different protein patterns and to different hereditary information which is associated with this. For example, some representatives of the poxviruses have the ability to agglutinate erythrocytes. This activity is mediated by way of a surface protein, the so-called haemagglutinin (HA). PPV do not possess this activity.

Knowledge of the organization of the PPV genome is currently restricted to determinations of the size of the genome, the GC content of the nucleic acid, comparative restriction enzyme analyses, the cloning of individual genome fragments, and sequence analyses of part regions and the associated preliminary description of individual genes (for a review, see Lit. #1, Lit. #5, Lit. #6).

It is not currently possible to use insertion sites which are known in the case of vaccinia due to the fact that these sites are either lacking or have not been demonstrated in PPV.

Thus, attempts to identify the gene for thymidine kinase in the PPV genome and to use it as an insertion site, as in the case of the orthopoxviruses, were not successful. While Mazur and coworkers (Lit. #3) describe the identification of a segment of the PPV genome which they claim resembles the thymidine kinase gene of vaccinia virus (an orthopoxvirus), our own extensive investigations have not been able to confirm the existence of such a gene in PPV. Other authors (Lit. #1) have also not been able to find a thymidine kinase gene in PPV. The gene for HA is used as an insertion site for foreign DNA in vaccinia virus. As described above, PPV do not possess this activity.

In 1992, Robinson and Lyttle mentioned alternative insertion sites on the PPV genome (Lit. #1) without, however, providing a description or a precise characterization of these sites. There has furthermore still not been any description of the successful use of PPV as vectors.

In our own analytical investigations of the sequence of HindIII fragment I from PPV strain D1701, we found an ORF which possesses amino acid homology (36.1 to 38.3% identity; 52.8 to 58.6% similarity, GCG, Wisconsin Package 8.1, e.g. Pikup Program) with vascular endothelial growth factor (VEGF) from various mammalian species (e.g. mouse, rat, guinea pig, cow and man). Seq. ID No: 1 shows the nucleotide sequence of the gene in D1701, while Seq. ID No: 15 shows the amino acid sequence of the corresponding D1701 protein. Recently, a homologous gene was also described in PPV strains NZ2 and NZ7 (Lit. #6); however the function of this gene is not known. Other poxviruses, e.g. orthopoxviruses, are not known to have a corresponding gene. In the remainder of the text, this gene is termed VEGF gene.

Our sequence analysis of HindIII fragment I of D1701 led to the identification of another ORF which possesses homology with orthopoxvirus protein kinase genes and is known in vaccinia as F10L. The identity with the vaccinia F10L gene is 51% while the similarity is 70%. In the remainder of the application, this gene is termed PK gene. Seq. ID No: 2, No: 9 and No: 13 show versions of the nucleotide sequence of the gene in D1701, while Seq. ID No: 14 shows the amino acid sequence of the corresponding D1701 protein.

An additional ORF was found which overlaps the 3' end of the PK gene and the 5' end of the VEGF gene. Homology investigations showed that there was low identity (28%) and low similarity (51%) with the F9L gene in vaccinia. Seq. ID No: 5 and No: 10 show versions of the nucleotide sequence of the gene in D1701. In the remainder of the text, this gene is termed the F9L gene.

A further ORF, which, due to its similarity to a gene in PPV NZ2 (identity 76%, similarity 83%), is termed ORF3, was found within the ITR region. Seq. ID No: 4 shows the nucleotide sequence of the gene in D1701. In the remainder of the text, this gene is termed ORF3 gene.

The present invention relates to

1. Recombinantly prepared PPV having insertions and/or deletions.
2. Recombinantly prepared PPV having insertions and/or deletions in genome segments which are not required for virus multiplication.
3. Recombinantly prepared PPV having insertions and/or deletions in genome segments which are required for virus multiplication.
4. Recombinantly prepared PPV which contain insertions and/or deletions in the regions of HindIII fragment I from D1701 which are not expressed.
5. Recombinantly prepared PPV which contain insertions and/or deletions in the regions of HindIII fragment I from D1701 which are expressed.
6. Recombinantly prepared PPV according to 1 to 5, in which insertions and/or deletions are located in D1701 HindIII fragment I or in the DNA from other PPV which corresponds to this fragment.
7. Recombinantly prepared PPV which contain insertions and/or deletions in the region of the VEGF gene or adjoining this region.
8. Recombinantly prepared PPV which contain insertions and/or deletions in the region of the PK gene or adjoining this region.
9. Recombinantly prepared PPV which contain insertions and/or deletions in the region of the ITR segment or adjoining this region.
10. Recombinantly prepared PPV which contain insertions and/or deletions in the region of the HD1R gene or adjoining this region.
11. Recombinantly prepared PPV which contain insertions and/or deletions in the region of the F9L gene or adjoining this region.
12. Recombinantly prepared PPV which contain insertions and/or deletions in the region, or in the vicinity, of the gene which encodes the 10 kDa protein.
13. Recombinantly prepared PPV which contain insertions and/or deletions in the region of EcoRI fragment E from D1701, in which the gene encoding the 10 kDa protein is located.
14. Plasmid which contains HindIII fragment I from D1701 or DNA from other PPV which corresponds to this fragment.
15. Plasmid which contains HindIII fragment I from D1701 and which, in this fragment, contains deletions and/or insertions in regions which are required for virus replication.
16. Plasmid which contains HindIII fragment I from D1701 and which, in this fragment, contains deletions and/or insertions in regions which are not required for virus replication.
17. Plasmid which contains HindIII fragment I from D1701 and which, in this fragment, contains deletions and/or insertions in the regions which are not required for virus replication and which are not expressed.
18. Plasmid which contains HindIII fragment I from D1701 and which, in this fragment, contains deletions and/or insertions in the regions which are not required for virus multiplication and which lie in regions which are expressed.
19. Plasmid which contains HindIII fragment I from D1701 and which contains deletions and/or insertions in, or adjacent to, the VEGF gene of this fragment.
20. Plasmid which contains HindIII fragment I from D1701 and which contains deletions and/or insertions in, or adjacent to, the PK gene of this fragment.
21. Plasmid which contains HindIII fragment I from D1701 and which contains deletions and/or insertions in, or adjacent to, the ITR segment of this fragment.
22. Plasmid which contains HindIII fragment I from D1701 and which contains deletions and/or insertions in, or adjacent to, the HD1R gene and/or the F9L gene.
23. Plasmid which contains EcoRI fragment E from D1701 and which contains deletions and/or insertions in, or adjacent to, the gene which encodes the 10 kDa protein.
24. Plasmid which contains part of HindIII fragment I from D1701 in which deletions and/or insertions in accordance with 14 to 23 are present.
25. Plasmid according to 14 to 24, in which the DNA fragment from D1701 is replaced with a DNA from other PPV which corresponds to this fragment.
26. Plasmid according to 14 to 25, which either contains the whole of HindIII fragment I or only a part of it.
27. D1701 HindIII fragment I, or parts thereof, or fragments from other PPV which correspond to this fragment, having the sequence according to sequence listing ID No: 8 or No: 12.
28. DNA segment or parts of D1701 HindIII fragment I, or the segment from other PPV which corresponds to this segment, or parts thereof, which encodes VEGF protein in accordance with sequence listing ID No: 1.
29. DNA segment or parts of D1701 HindIII fragment I, or the segment from other PPV which corresponds to this segment or parts thereof, which encodes PK protein according to sequence listing ID No: 2, No: 9 or No: 13.
30. DNA segment, or parts thereof, for the HD1R gene having the sequence according to sequence listing ID No: 3 of PPV.
31. DNA segment, or parts thereof, for F9L having the sequence according to sequence listing ID No: 5 or ID No: 10 of PPV.
32. DNA segment, or parts thereof, for the ITR region having the sequence according to sequence listing ID No: 4 of PPV.
33. Gene products which have been prepared on the basis of the sequences of the DNA segments according to 27 to 32.
34. Recombinantly prepared PPV according to 1 to 13 which contain, as insertions, foreign DNA which encodes immunogenic constituents from other pathogens.
35. Recombinantly prepared PPV according to 1 to 13 and 34 which contain, as insertions, foreign DNA which encodes cytokines.
36. Process for preparing the viruses according to 1 to 13, 34 and 35, characterized in that the plasmids according to 14 to 26 are recombined with PPV in cells in the manner known per se and selected for the desired viruses.

37. Process for preparing the plasmids according to 23, characterized in that
   1. a suitable PPV strain is selected,
   2. its genome is purified,
   3. the purified genome is treated with restriction enzymes,
   4. the resulting fragments are inserted into plasmids, and
   5. selection is carried out for the plasmids which contain the gene which encodes the 10 kDa protein, and
   6. where appropriate, insertions and/or deletions are introduced into the gene encoding the 10 kDa protein,
   7. the fragments described under 4 (above) can, where appropriate, also be prepared using alternative methods such as polymerase chain reaction (PCR) or oligonucleotide synthesis.

38. Process for preparing the plasmids according to 14 to 22 and 24 to 26, characterized in that
   1. a suitable PPV strain is selected,
   2. its genome is purified,
   3. the purified genome is treated with restriction enzymes,
   4. the resulting fragments are inserted into plasmids, and
   5. selection is carried out for the plasmids which contain HindIII fragment I or fragments or constituents which correspond to this fragment,
   6. and, where appropriate, insertions and/or deletions are introduced into these fragments in the resulting plasmids.
   7. the fragments described under 4 (above) can, where appropriate, also be prepared using alternative methods such as polymerase chain reaction (PCR) or oligonucleotide synthesis.

39. Process for preparing D1701 HindIII fragment I or EcoRI fragment E, which encodes the 10 kDa protein, or the region from other PPV which corresponds to this fragment or segment, or parts thereof, characterized in that
   1. a suitable PPV strain is selected,
   2. its genome is purified,
   3. the purified genome is treated with restriction enzymes,
   4. and the desired fragments or segments are selected, or
   5. where appropriate, the resulting fragments of the genome are initially inserted in plasmids and the plasmids containing the desired fragments are isolated, after which these plasmids are multiplied and the desired fragments are isolated from them.
   6. the fragments described under 4 (above) can, where appropriate, also be prepared using alternative methods such as PCR or oligonucleotide synthesis.

40. Process for preparing the gene products according to 33, characterized in that the fragments obtainable in accordance with 39 are transferred into suitable expression systems and the genes are expressed using these systems.

41. Use of the recombinantly prepared PPV according to 1 to 13 in vaccines.

42. Use of the recombinantly prepared PPV according to 1 to 13 in products which both immunize and stimulate non-pathogen-specific immune defence.

43. Use of the recombinantly prepared PPV in immunomodulators which stimulate non-pathogen-specific immune defence.

44. Use of the recombinantly prepared PPV for heterologously expressing foreign DNA.

45. Use of the recombinantly prepared PPV as vectors for foreign DNA.

46. Use of the plasmids according to 14 to 16 for expressing parapox-specific genome segments.

47. Use of the plasmids according to 14 to 26 for preparing diagnostic agents.

48. Use of the genome fragments according to 27 to 32 for preparing diagnostic agents.

49. DNA segments according to sequence listing ID No: 6 (promoter of the VEGF gene).

50. Use of the DNA segment according to 49 as a promoter for expressing DNA.

The above-described genome fragments of PPV, which can be inserted into plasmids or viruses and which can be present as free DNA segments, encompass the given DNA sequences and their variants and homologs.

The above-listed terms have the following meanings:

Attenuation is a
   process in which, as a result of an alteration to their genome, the PPV have become less pathogenic or not pathogenic, or less virulent or not virulent, for animals or man.

Deletions are
   pieces of DNA which are missing from the PPV genome.

Deletion plasmids are
   plasmids which, in addition to the plasmid DNA, carry segments of the PPV genome from which pieces have been removed.

Genome segments which are necessary (essential) for virus multiplication are
   parts of the whole PPV genome which are indispensable for the in-vitro multiplication of PPV, i.e. are indispensable for forming infectious virus progeny.
   Interference with genes which are essential for virus multiplication leads to the virus multiplication being interrupted. If, for example, parts of one of these genes, or the entire gene, is removed, replication of the virus terminates at a defined point in the multiplication cycle of the virus. Infection or treatment with mutants of this nature do not lead to any release of infectious progeny from the animal. If parts of an essential gene, or a whole essential gene, is/are replaced with foreign DNA, or if foreign DNA is inserted into essential genes, it is possible to construct vector vaccines which are unable to multiply in the vaccinated individual and which are consequently not excreted as infectious pathogens.

Genome segments which are not required (nonessential) for virus multiplication are
   parts of the whole PPV genome which can be dispensed with for the in-vitro multiplication of PPV, i.e. for forming infectious virus progeny.

Foreign DNA elements (foreign DNA) are
   DNA pieces, e.g. foreign genes or nucleotides sequences, which are not originally present in the PPV which is employed in accordance with the invention.
   Foreign DNA is inserted into the PPV for the following reasons:
   1. for expressing the foreign DNA
   2. for inactivating functions of pieces of the PPV DNA
   3. for labelling the PPV.
   Depending on these reasons, different foreign DNA is inserted. If foreign DNA is to be expressed in accordance with (1), the inserted foreign DNA will at least carry an open reading frame which encodes one or more desired foreign protein(s). Where appropriate, the foreign DNA additionally contains its own or foreign regulatory sequences. The capacity for taking up foreign DNA can be increased by creating deletions in the genome of the virus. In general, the length is between 1 nucleotide and 35,000 nucleotides, preferably between 100 and about 15,000 nucleotides.

Examples which may be mentioned are genes, or parts of genes, from viruses such as
Herpesvirus suid 1,
Equine herpesviruses
Bovine herpesviruses
Foot and mouth disease virus,
Bovine respiratory syncytial virus,
Bovine parainfluenza virus 3,
Influenza virus
Calicivirus
Flaviviruses, e.g. bovine virus diarrhoea virus or classical swine fever virus
or of bacteria, such as
Pasteurella spec.,
Salmonella spec.,
Actinobacillus spec.,
Chlamydia spec.,
or of parasites, such as
Toxoplasma,
Dirofilaria,
Echinococcus.

If foreign DNA is to be inserted in accordance with (2), the insertion of a suitable foreign nucleotide is in principle sufficient for interrupting the DNA sequence of the vector virus. The maximum length of the foreign DNA which is inserted for the inactivation depends on the capacity of the vector virus to take up foreign DNA. In general, the length of the foreign DNA is between 1 nucleotide and 35,000 nucleotides, preferably between 100 and 15,000 nucleotides, particularly preferably between 3 and 100 nucleotides.

If DNA sequences are to be inserted for labelling in accordance with (3), their length depends on the detection method used for identifying the labelled virus. In general, the length of the foreign DNA is between 1 and 25,000 nucleotides, preferably between 20 nucleotides and 15,000 nucleotides, particularly preferably between 5 and 100 nucleotides.

Gene library
is the entirety of the fragments of a genome which are contained in vectors which are capable of replication. The library is obtained by fragmenting the genome and inserting all the fragments, a few of the fragments or a major part of the fragments into vectors which are capable of replicating, for example plasmids.

A genome fragment is
a piece of a genome which can be present in isolated form or can be inserted into a vector which is capable of replicating.

Inactivation by insertion means
that the inserted foreign DNA prevents the native PPV genome sequences from being expressed or from functioning.

Insertions are
pieces of DNA which have been additionally incorporated into the PPV genome. Depending on the reason for the insertion, the length of the DNA pieces can be between 1 nucleotide and several thousand nucleotides (see definition of "foreign DNA" as well).

Insertion plasmids are
plasmids, in particular bacterial plasmids, which contain the foreign DNA to be inserted flanked by PPV DNA sequences.

Insertion sites are
sites in a viral genome which are suitable for receiving foreign DNA.

Cloning means
that the PPV genomic DNA is isolated and fragmented. The fragments, or a selections of the fragments, is/are then inserted into customary DNA vectors (bacterial plasmids or phage vectors or eukaryotic vectors).
Lit. #11 provides a selection of methods for preparing and cloning DNA fragments. The DNA vectors, containing the PPV DNA fragments as inserts, are used, for example, for preparing identical copies of the originally isolated PPV DNA fragments.

Labelling by insertion means
that the inserted foreign DNA enables the modified PPV to be subsequently identified.

ORF (open reading frame) is understood as meaning a sequence of nucleotides, at the DNA level, which defines the amino acid sequence of a potential protein. It consists of a number, which is determined by the size of the protein which it defines, of nucleotide triplets which is delimited at the 5' end by a start codon (ATG) and at the 3' end by a stop codon (TAG, TGA or TAA).

Regulatory sequences are
DNA sequences which exert an effect on the expression of genes. Sequences of this nature are known from Lit. #15.
Preference may be given to mentioning the VEGF promoter as described in sequence listing ID No: 6.

Recombinant PPV are
PPV having insertions and/or deletions in their genome. In this connection, the insertions and deletions are prepared using molecular biological methods.

Repetitive (DNA) sequences are
identical nucleotide sequences which occur in the PPV genome either directly one after the other or scattered at different sites.

Vector virus is
a PPV which is suitable for the insertion of foreign DNA and which can transport the inserted foreign DNA, in its genome, into infected cells or organisms, and which, where appropriate, enables the foreign DNA to be expressed.

The novel PPV according to 1 to 12 (above) are prepared as follows:
1. Selection of a suitable PPV strain
2. Identification of genome segments in the PPV genome which possess insertion sites
2.a Identification of PPV genome segments possessing insertion sites in genes which are non-essential for virus multiplication,
2.b Identification of PPV genome segments possessing insertion sites in genes which are essential for virus multiplication,
2.c Identification of genome segments possessing insertion sites in regions outwith genes in the PPV genome and/or in gene duplications 2.d Other methods for identifying genome segments possessing insertion sites
2.e Demands placed on an insertion site
2.1 Identification of insertion sites
2.1.1 Purification of the PPV genome
2.1.2 Cloning the genome fragments and establishing a gene library
2.1.3 Sequencing for the purpose of identifying genes or genome segments outwith genes
2.1.4 Selection of the clones containing PPV genome fragments for further processing
2.2 ITR region, VEGF gene, PK gene, gene encoding the 10 kDa protein, and the region between the PK gene and the HD1R gene, as insertion sites
2.2.1 Cloning the VEGF gene
2.2.2 Cloning the protein kinase gene
2.2.3 Cloning the gene region which encodes the 10 kDa protein
2.2.4 Cloning the ITR region (inverted terminal repeat region) or the genome segment which lies between the PK gene and the HD1R gene
3. Construction of insertion plasmids or deletion plasmids which contain the foreign DNA to be inserted,
3.1 Identifying or preparing restriction enzyme recognition sites which only occur once, i.e. unique restriction sites, in the cloned genome fragments and inserting foreign DNA
3.2 Deleting genome sequences in the cloned genome fragments and inserting foreign DNA
3.3 A combination of #3.1 and #3.2
4. Construction of a recombinant PPV in accordance with 1 to 12 (above).
1. Selection of a suitable PPV strain In principle, all PPV species are suitable for implementing the present invention. Virus strains are preferred which can be multiplied to titres >$10^5$ PFU (plaque forming unit)/ml in a tissue culture and which can be prepared in pure form as extracellular, infectious virus, from the medium of the infected cells. The species from the PPV genus which may be mentioned as being prefer red is PPV ovis (orf viruses).

The strain of PPV ovis which may be mentioned as being particularly preferred is D1701, which was deposited on 28.04.1988, in accordance with the Budapest Treaty, at Institut Pasteur, C.N.C.M. under Reg. No. CNCM I-751, and also its variants and mutants.

The viruses are multiplied in a customary manner in tissue cultures of animal cells such as mammalian cells, e.g. in sheep cells or bovine cells, preferably in bovine cells such as the permanent bovine kidney cell line BK-K1-3A (or its descendants) or monkey cells, such as the permanent monkey kidney cells MA104 or Vero (or their descendants).

The multiplication is effected, in a manner known per se, in stationary, roller or carrier cultures in the form of compact cell aggregates or in suspension cultures.

The cells or cell lawns which are used for multiplying the viruses are multiplied virtually to confluence or up to optimal cell density in a customary manner. The cells are infected with virus dilutions which correspond to an MOI (=multiplicity of infection, corresponds to infectious virus particles per cell).

The viruses are multiplied with or without the addition of animal sera. When serum is employed, it is added to the multiplication medium at a concentration of 1–30 vol %, preferably 1–10 vol %.

Infection and virus multiplication are carried out at temperatures of between room temperature and 40° C., preferably between 32 and 39° C., particularly preferably at 37° C., over several days, preferably until the infected cells have been completely destroyed. In association with harvesting the virus, virus which is still cell-bound can additionally be released mechanically or by means of ultrasonication or by means of mild enzymic proteolysis, for example using trypsin.

The virus-containing medium from the infected cells can then be worked up further, for example by removing the cell debris by means of filtration using pore sizes of, for example, 0.2–0.45 µm and/or low-speed centrifugation.

Filtrates or centrifugation supernatants can be used for virus enrichment and purification. For this, filtrates or supernatants are subjected to high speed centrifugation until the virus particles sediment. Where appropriate, further purification steps can follow, for example by means of centrifugation in a density gradient.

2. Identification of genome segments possessing insertion sites in the PPV genome Various regions of the PPV genome can be used as insertion sites when inserting foreign DNA. Foreign DNA can be inserted a. into genes which are non-essential for virus multiplication in vitro and/or in vivo, b. into genes which are essential for virus multiplication, and/or c. in regions which do not possess any gene function.

2.a Identification of genome segments in the PPV genome which possess insertion sites in genes which are not essential for virus multiplication i. Viral genes which are not essential for multiplication of the virus are found, for example, by means of carrying out comparative investigations using representatives of different PPV species. Genes which do not occur in one or more isolates or strains of a PPV species but which are found in other isolates or strains are potentially non-essential.

ii. Genes which are not essential for virus multiplication can also be identified in an alternative manner. After PPV genome fragments, which may, for example, be present as cloned fragments, have been sequenced, these DNA sequences are examined for possible "open reading frames" (ORF). If an ORF is found, the function of this ORF as a gene is verified by demonstrating transcription and/or translation. In order to establish whether the gene which has been found is non-essential for virus multiplication, molecular genetic methods are used to remove the gene from the PPV genome, or to destroy it partially or to interrupt it by means of introducing (a) mutation(s), and the ability of the resulting virus to multiply is then investigated. If the virus is able to replicate even without the existence of the manipulated gene, the latter is a non-essential gene.

Examples of identified insertion sites i. The VEGF gene of PPV ovis may be mentioned at this point as an example of a non-essential PPV gene which can be used as an insertion site for foreign DNA. This gene is found in the Parapoxvirus ovis strains (NZ-2, NZ-7 and D1701) which have been investigated (Lit. #6). This VEGF gene has not been demonstrated in some PPV strains, for example representatives of PPV bovis 1. The region on the PPV genome containing the VEGF gene can be identified with the aid of the DNA sequence shown in sequence listing ID No: 1. The customary methods of molecular biology can be used to find the gene on the genome of a PPV by means of hybridization experiments, genome sequence analyses and/or polymerase chain reactions.

ii. The gene for the 10 kDa PPV protein may be mentioned as another example of a potentially non-essential PPV gene. This gene is found in strains of Parapoxvirus ovis (NZ-2, NZ-7 and D1701). Customary methods of molecular biology can be used to identify the region on the PPV genome which contains the gene for the 10 kDa protein, for example by means of polymerase chain reactions (PCR). Lit. #8 gives the DNA sequence of the 10 kDa protein gene. The primers which can be used for a PCR are specified, for example, in Lit. #8. Sequence listing ID No: 11 shows the DNA sequence of the 10 kDa-specific PCR product from D1701.

For the purpose of inserting foreign DNA, the non-essential gene can be removed from the PPV genome either in parts or entirely. However, it is also possible to insert foreign DNA into the non-essential gene without removing any regions of the PPV gene. Restriction enzyme recognition sites can, for example, be used as insertion sites.

2.b. Identification of PPV genome segments, on the PPV genome, which possess insertion sites in genes which are essential i. Essential genes can be identified by sequencing viral genome fragments, which are, for example, present as cloned fragments, and then identifying possible ORFs. If an ORF is found, its function as a gene is verified by demonstrating transcription and/or translation. In order to establish whether the gene has been found is essential for virus multiplication, molecular genetic methods are used to destroy the gene in the PPV genome, for example by removing parts of the gene, or the entire gene, or by means of inserting foreign DNA, and then investigating the ability of the resulting virus to multiply.

If the resulting virus mutant is unable to replicate, the gene is then very probably an essential gene.

If the virus mutant is only able to grow on complementing cell lines, this then proves that the gene is essential.

Examples of insertion sites

The protein kinase gene (PK gene) of PPV D1701 may be mentioned as an example. The PK gene is expressed late in the multiplication cycle of the virus. The versions of the DNA sequence shown in sequence listing ID No: 2, No: 9 or No: 13 can be used to identify the PK gene on the PPV genome. The customary methods of molecular biology can be used to find the region containing the gene, for example by means of hybridization experiments, genome sequence analyses and/or polymerase chain reactions.

For the purpose of inserting foreign DNA, the essential gene can be removed, either in parts or entirely, from the PPV genome. However, it is also possible to insert the foreign DNA into the essential gene without removing regions from the PPV gene.

2.c Identification of genome segments on the PPV genome possessing insertion sites in regions outwith genes and/or in gene duplications Genome segments which do not encode functional gene products and which do not possess any essential regulatory functions (so-called intergenic segments) are, in principle, suitable for use as insertion sites for foreign DNA. Regions containing repetitive sequences are particularly suitable, since changes in parts of a region can be offset by sequence repetitions which remain. Genes which occur in two or more copies, so-called gene duplications, also come within this category.

Genes in the ITR region or in duplicated segments of the PPV genome exist in two copies in the viral genome. After one copy of such a gene has been removed or altered, and foreign DNA has been inserted, stable PPV recombinants can be obtained even if the altered gene is important for virus multiplication. A second, unaltered gene copy may be adequate for the function of the gene.

i. Sequence analyses of the PPV genome are used to identify genome sequences which do not encode gene products. Genome regions which do not exhibit either an ORF after sequence analysis or virus-specific transcription and which do not possess any regulatory function represent potential insertion sites. In particular, the cleavage sites for restriction enzymes in these regions represent potential insertion sites. In order to check whether a suitable insertion site is present, known molecular biological methods are used to insert foreign DNA into the potential insertion site, and the viability of the resulting virus mutant is then investigated. If the virus mutant which carries foreign DNA in the possible insertion site is capable of multiplication, the site being investigated is a suitable insertion site.

ii. DNA hybridization experiments and/or sequence analyses are used to identify repetitive sequences and gene duplications. In the hybridization experiments, cloned or isolated genome fragments from a PPV are used as probes for hybridizations with fragments of PPV DNA. The genome fragments of the PPV which hybridize with more than one fragment of the total PPV genome contain one or more repetitive sequences. In order to locate the repetitive sequence or the duplicated genome regions accurately on the genome fragment, the nucleotide sequence of this fragment is determined. In order to establish whether a potential insertion site is a suitable insertion site in the whole PPV genome, foreign DNA has to be inserted into a repetitive sequence or into a copy of the gene duplication and the PPV genome fragment containing the insert has to be incorporated into the viral genome. The ability of the recombinant virus containing the foreign DNA to multiply is then examined. If the recombinant virus multiplies, the identified recognition site is suitable as an insertion site.

Examples of insertion sites i. The genome segment between the gene for the protein kinase and the HD1R gene (sequence listing ID No: 7) may be mentioned as an example of an intergenic region.

ii. The ITR region (sequence listing ID No: 4) may be mentioned as an example of a repetitive sequence.

iii. The potential gene "ORF 3" (in the ITR region) and the VEGF gene may be mentioned as examples of gene duplications in PPV strain D1701. Hybridization studies demonstrated that a region containing the VEGF gene has been duplicated in the present strain D1701 and translocated to the other end of the virus genome, so that two copies of the VEGF gene are present.

With the aid of the sequences in sequence listing ID No: 4 (ITR sequence with "ORF3" gene) and ID No: 7 (region between PK and HD1R genes), customary methods of molecular biology, such as hybridization experiments, genome sequence analyses and/or polymerase chain reactions, can be used to find the corresponding genome regions in other PPV.

2.d Other methods for identifying insertion sites

In general, modifications of the viral genome sequences can also be used to find possible insertion sites on the PPV genome. Genome sites at which nucleotide substitutions, deletions and/or insertions, or combinations thereof, do not block virus multiplication constitute possible insertion sites. In order to check whether a potential insertion site is a suitable insertion site, known molecular biological methods are used to insert foreign DNA into the potential insertion site and the viability of the resulting virus mutant is investigated. If the virus recombinant is able to multiply, the site under investigation is a suitable insertion site.

2.1 Identification of insertion sites 2.1.1 Purification of the PPV genome

For the purpose of cloning PPV insertion sites by means of molecular genetics, the PPV genome is first of all purified. The genome is isolated from the virus prepared in accordance with 1 (above) and then purified. Native viral DNA is preferably extracted by treating the purified virions with aqueous solutions of detergents and proteases.

Detergents which may be mentioned are anionic, cationic, amphoteric and nonionic detergents. Preference is given to using ionic detergents. Sodium dodecyl sulphate (sodium lauryl sulphate) is particularly preferred.

Proteases which may be mentioned are all proteases which function in the presence of detergents, such as proteinase K and pronase. Proteinase K may be mentioned as being preferred.

Detergents are employed in concentrations of 0.1–10 vol %, with 0.5–3 vol % being preferred.

Proteases are employed in concentrations of 0.01–10 mg/ml of virus lysate, with 0.05–0.5 mg/ml of virus lysate being preferred.

Preference is given to carrying out the reaction in an aqueous buffered solution in the presence of DNase inhibitors. Buffering substances which may be mentioned are: salts of weak acids with strong bases, e.g. tris (hydroxymethylaminomethane), salts of strong acids with weak bases, e.g. primary phosphates, or mixtures thereof.

The following buffer system may be mentioned as being preferred: tris(hydroxymethylaminomethane).

The buffering substances or buffering systems are employed at concentrations which ensure pH values at which the DNA does not denature. Preference is given to pH values of 5–9, with particular preference being given to values of 6–8.5 and very particular preference being given to values of 7–8; operating in the neutral range may be mentioned, in particular.

An example of a DNase inhibitor is ethylenediaminetetraacetic acid at concentrations of 0.1–10 mM (millimole), with approx. 1 mM being preferred.

After that, the lipophilic components of the virus lysate are extracted. Solvents such as phenol, chloroform, isoamyl alcohol, or their mixtures, are used as extracting agents. Preference is given to using a mixture of phenol and chloroform/isoamyl alcohol initially, with the extraction taking place in one or more stages.

Examples of other methods for isolating virus DNA are centrifugation of a virus lysate in a CsCl density gradient or gel electrophoresis (see Lit. #14).

The extraction of nucleic acids is described in Lit. #13.

The DNA which has been extracted in this way is preferably precipitated from the aqueous solution with, for example, alcohol, preferably with ethanol or isopropanol, and in the added presence of monovalent salts such as alkali metal chlorides or acetates, preferably lithium chloride, sodium chloride, or sodium acetate or potassium acetate (see loc. cit.).

2.1.2 Cloning the genome fragments

The viral DNA which has been purified in this way is now used to prepare DNA fragments. For this, it is, for example, treated with restriction enzymes. Examples of suitable restriction enzymes are EcoRI, BamHI, HindIII and KpnI. Alternatively, genome fragments can be synthesized by means of the polymerase chain reaction (PCR). For this, primers are selected from sequence segments of the viral genome which are already known, and the genome segment which is delimited by the primer pair is synthesized in vitro using, for example, Taq polymerase or Pfu polymerase.

The DNA fragments resulting from restriction digestion or PCR can be cloned into vector systems using the methods described in (Sambrook 89). For example, depending on the size of the DNA fragment to be cloned in each case, plasmid vectors, lambda phage vectors or cosmid vectors are available for this purpose.

2.1.3 Sequencing, identifying and characterizing genes, and verifying their expression Genome fragments which are cloned into vectors are first of all analyzed by sequencing. The inserted DNA fragments are mapped using different restriction enzymes and suitable subfragments are cloned into plasmid vectors. The sequencing reaction is effected, for example, using the T7 Sequencing Kit supplied by Pharmacia in accordance with the manufacturer's instructions. The double-stranded plasmid DNA which is required for this is preferably prepared using the PEG method (Hattori and Sakaki 1985). "Open reading frames (ORF)" which are present in the genome fragments are identified by means of computer analysis (GCG, see above). Information about the respective function of the identified ORFs can be obtained by means of comparing their sequences with other gene sequences of known function which are contained in a database. The identified ORFs are functionally characterized by detecting their respective corresponding transcripts in virus-infected cells. For this, the AGPC method (Chomczynski and Sacchi, (20) 1987) is, for example, used to isolate the total RNA from virus-infected cells. The specific transcripts, and their 5' and 3' ends, can then be identified by means of Northern blot analysis or primer extension and RNA protection experiments. As an alternative, it is possible to express the virus protein which is encoded by an identified ORF in vitro, then to use the expression product to obtain antisera and to use these antisera to demonstrate expression of the ORF.

In order to establish whether the gene which has been found is non-essential for virus multiplication, the gene can be destroyed by means of gene disruption or gene deletion. In this context, either the entire gene, or parts of it, are removed from the PPV genome or the reading frame of the gene is interrupted by inserting foreign gene sequences. The ability of the resulting virus to multiply is examined. If the virus can replicate even without the existence of the destroyed gene, this gene is then a non-essential gene.

2.1.4 Selecting the clones containing PPV genome fragments

Which of the PPV genome fragment-containing clones obtained above are employed depends on whether the recombinant PPV which are to be prepared are to be (i) capable of replication or (ii) defective in their replication.

i. If recombinant PPV are to be prepared which are capable of replication despite the insertion and/or deletion, further processing is carried out on cloned viral genome fragments which contain genes or genome regions outwith genes which are non-essential for virus multiplication or which contain gene duplications.

Virus mutants are used to test whether the gene or genome region to hand is a non-essential region of the virus genome or a gene duplication. For this, molecular biological methods are used to inactivate the gene or genome region in the PPV which is being investigated, for example by partially or completely deleting the region in question, and the ability of the virus mutant to multiply is examined. If the virus mutant can multiply despite the gene or genome region in question having been inactivated, the gene or genome region under investigation is a non-essential region.

Preference is given to cloned genome fragments of the PPV which contain complete versions of the non-essential genes. In addition to this, the flanking viral genome regions at both ends of the genes or the genome regions should also be present. The length of the flanking regions should be more than 100 base pairs. If such genome clones are not available, they can be prepared from existing gene clones by means of molecular biological methods. If the cloned genome fragments additionally contain genome regions which are not required for the present preparation, these regions can be removed by means of subclonings.

ii. If recombinant PPV are to be prepared which have lost the ability to form infectious progeny as a result of the insertion and/or deletion, cloned viral genome fragments which contain genes or genome regions outwith genes which are essential for virus multiplication are subject to further processing.

Virus mutants can be used to test whether the gene or genome region to hand is an essential region of the virus genome. For this, molecular biological methods are used to inactivate the gene or the genome region in the PPV under investigation, for example by partially or completely deleting the region in question, and the ability of the virus mutant to multiply is examined. If the virus mutant can no longer multiply as a result of the gene or genome region in question having been inactivated, the gene or genome region under investigation is an essential region.

Preference is given to cloned genome fragments of the PPV which contain complete versions of the essential genes. In addition to this, the flanking viral genome regions should likewise be present at both ends of the genes or the genome regions. The length of the flanking regions should be more than 100 base pairs. If such genome clones are not available, they can be prepared from existing genome clones by means of molecular biological methods. If the cloned genome fragments contain additional genome regions which are not required for the present preparation, these regions can be removed by means of subclonings.

2.2 ITR region, VEGF gene, PK gene, gene encoding the 10 kDa protein, and the region between the PK gene and the HD1R gene, as insertion sites If the ITR region, the VEGF gene, the PK gene, the gene which encodes the 10 kDa protein, or the intergenic region between the PK gene and the HD1R gene, is to be used as an insertion site in a PPV, the corresponding regions of the PPV genome, which contain the insertion sites, have to be isolated. For this, the corresponding regions of the PPV genome are cloned.

2.2.1 Cloning the VEGF gene

The gene which encodes VEGF is located on the PPV genome and is then isolated in parts or in its entirety together with its flanking genome segments. For this, the PPV is preferably multiplied in accordance with #1 and the genome is purified in accordance with #2.1.1.

a. The VEGF gene is preferably amplified by means of a polymerase chain reaction (PCR). The start sequences (primers) which are required for this reaction are derived from the DNA sequence of the VEGF gene which is depicted in sequence listing ID No: 1. The resulting amplificate is then preferably cloned.

b. The region which contains the VEGF gene and its flanking genome segments is preferably obtained by fragmenting the PPV genome and isolating and cloning the corresponding genome fragment(s). For this, the purified genome of the virus is cleaved as described in #2.1.2, preferably using the restriction enzyme HindIII. The genome fragments which are obtained after the enzyme digestion are preferably fractionated by means of electrophoretic or chromatographic methods in order to identify the genome fragment(s) which carries/carry the VEGF gene and its flanking genome segments.

Electrophoretic fractionations in agarose or polyacrylamide are carried out using standard methods which are described in Current Protocols in Molecular Biology 1987–1988, Wiley-Interscience, 1987.

A Practical Guide to Molecular Cloning, Perbal, 2nd edition, Wiley Interscience, 1988

Molecular Cloning, loc. cit.

Virologische Arbeitsmethoden [Practical Methods in Virology], Volume III, Gustav Fischer Verlag, 1989.

The genome fragments which carry the VEGF gene and its flanking sequences are identified, for example, by means of hybridization with defined nucleic acid probes. For this, the fractionated genome fragments are transferred to filters and hybridized with VEGF-specific, labelled nucleic acid probes in accordance with the Southern blot method. The methods for transferring the genome fragments and for the hybridization can be carried out in accordance with standard protocols, as described under "Southern Blotting" in Molecular Cloning loc. cit. The oligonucleotides or nucleic acid fragments which can be used as probes can be derived from sequence listing Seq ID No: 1. For example, the TaqI subfragment (366 bp), which can be identified by means of Seq ID No: 1, is employed as a hybridization probe.

The genome fragments which have been demonstrated to contain parts, or preferably the whole, of the VEGF gene and the flanking genome segments, are isolated and cloned. The appropriate genome fragment(s) is/are electrophoretically isolated, for example, from the appropriate region of the gel by means of electroelution or by using the low-melting agarose method.

In order to clone the VEGF gene, the genome fragments which have been prepared above are inserted into bacterial or eukaryotic vectors. Plasmid or phage vectors are particularly preferred initially. In order to insert the genome fragment, double-stranded plasmid or phage vector DNA molecules are treated with restriction enzymes so that suitable ends are produced for the insertion.

Known plasmids, such as pBR322 and its derivatives, e.g. pSPT18/19, pAT153, pACYC 184, pUC18/19 and pSP64/65, are used as plasmids.

The known variants of phage lambda, such as phage lambda ZAP and phage lambda gt10/11, or phage M13mp18/19, are, for example, used as phage vectors.

The restriction enzymes which can be used are known, for example, from Gene volume 92 (1989) Elsevier Science Publishers BV Amsterdam.

The plasmid or the phage vector which has been treated with restriction enzyme is mixed with an excess of the DNA fragment to be inserted, for example in an approximate ratio of 5:1, after which the mixture is treated with DNA ligase to ligate the fragment into the vector. In order to propagate the plasmid or phages, the ligation mixture is introduced into prokaryotic or eukaryotic cells, preferably into bacteria (e.g. Escherichia coli strain K12 and its derivatives) and the latter are replicated.

The bacteria are transformed and selected as described in Molecular Cloning loc. cit.

The identity of the foreign DNA is preferably verified by means of hybridization experiments and particularly preferably by means of sequence analyses. Subclonings are performed where appropriate.

2.2.2 Cloning the protein kinase gene

The gene which encodes the protein kinase is located on the PPV genome and then isolated in parts or in its entirety together with its flanking genome segments.

As described for the cloning of the VEGF gene, this region can be isolated by fragmenting the PPV genome (cleavage sites, see FIG. 1), preferably followed by cloning the fragments and selecting the fragments or clones which contain parts of the PK gene or, preferably, the entire PK gene together with flanking DNA sequences of the PPV genome. DNA molecules which can be employed as primers for a PCR or as probes for a hybridization can be derived from sequence listing ID No: 2 or ID No: 9.

Subclonings are performed where appropriate.

2.2.3 Cloning the gene which encodes the 10 kDa protein

The gene which encodes the 10 kDa protein is located on the PPV genome using the method described (above) in detail for the VEGF gene and the PK gene and isolated in parts or, preferably, in its entirety together with its flanking PPV genome sequences.

In this case, the region of the PPV genome which contains the gene for the 10 kDa protein, or parts thereof, is obtained, preferably by means of PCR and/or cloning and identifying and selecting the suitable clones.

Lit. #8 provides details of DNA molecules which can be employed as primers for a PCR or as probes for a hybridization. Subclonings are performed where appropriate.

2.2.4 Cloning the inverted terminal repeat region for the genome segment which lies between the PK gene and the HD1R gene The approach corresponds to the cloning of the VEGF gene which has been described in detail (above). The DNA molecules which can be employed, as primers for a PCR or as probes for a hybridization, for isolating the appropriate regions are evident from sequencing listing ID No: 4 (ITR region) and No: 7 (region between the PK gene and the HD1R gene).

3. Construction of insertion plasmids or deletion plasmids

So-called insertion plasmids, which can be used for inserting foreign DNA into the PPV genome, are prepared on the basis of the PPV genome fragments which are identified, located and cloned as described in Section 2. The insertion plasmids carry the foreign DNA which is to be inserted into the PPV, flanked by segments of the PPV genome. There are various options for preparing insertion plasmids: the following may be mentioned here as examples:

3.1 Identification or preparation of unique restriction enzyme recognition sites in the cloned genome fragments which are obtained as described in 2.1.4 or 2.2, and insertion of foreign DNA Restriction cleavage sites which only occur once, i.e. are unique, can, for example (see 2.1.3), be identified in the PPV nucleotide sequences which have been determined.

Synthetically prepared oligonucleotides which carry new unique cleavage sites for restriction enzymes can be incorporated into these unique restriction sites.

The resulting plasmids are propagated and selected as described previously.

Alternatively, PCR can be used, as described by Jacobs et al. (Lit. #12), to incorporate new unique restriction enzyme recognition sites into the PPV genome fragments.

The unique restriction enzyme recognition sites which have been identified and/or prepared are used for inserting foreign DNA into the PPV genome.

The foreign DNA is inserted using known methods (Lit. #11).

3.2 Deletion of genome sequences in the cloned genome fragments and insertion of foreign DNA Subfragments can, for example, be deleted from the cloned PPV genome fragments by treating the latter with restriction enzymes which preferably possess more than one, particularly preferably 2, recognition sites. After the enzyme treatment, the resulting fragments are fractionated as described above, for example electrophoretically, and isolated, and the appropriate fragments are joined together once again by means of ligase treatment. The resulting plasmids are propagated and the deleted plasmids are selected.

Alternatively, a unique restriction enzyme recognition site on the PPV genome fragment is used as the starting point for bidirectionally degrading the fragment with an endonuclease, for example the enzyme Bal31. The size of the deletion can be determined by the period during which the enzyme acts and can be checked by means of gel electrophoresis. Synthetic oligonucleotides are ligated to the newly produced fragment ends as described under 3.1 (above).

The foreign gene is transferred into the PPV genome in only a small percentage of the entire PPV population.

For this reason, selection systems are required to separate recombinant PPV from wild-type PPV (Lit. #16).

Preference is given to using the gpt selection system, which is based on the *E. coli* guanyl-phosphoribosyl transferase gene. When expressed in a eukaryotic cell, this gene confers resistance to mycophenolic acid, which is an inhibitor of purine metabolism. Its use in the construction of recombinant vector viruses has been described many times (see Lit. #16/#17).

4. Construction of a recombinant PPV in accordance with 1 to 12

Foreign DNA is inserted into the PPV genome by:

a. simultaneously transfecting the DNA of the insertion or deletion plasmid and infecting with PPV in suitable host cells, b. transfecting the DNA of the insertion or deletion plasmid and then infecting with the PPV in suitable host cells, c. infecting the PPV and then transfecting with the DNA of the insertion or deletion plasmid in suitable host cells.

The methods for the procedures which are suitable for this purpose are known. The transfection can be effected using known methods such as the calcium phosphate technique, liposome-mediated transfection or electroporation (see Lit. #18).

1. Infection with PPV:

Cell cultures which permit good virus multiplication and efficient transfection, for example the permanent bovine kidney cell line BK-K1-3A, are preferred for preparing PPV containing foreign DNA.

2. Preparation of the insertion or deletion plasmid DNA:
The transformed cells, for example bacteria, which were obtained by the previously described methods and which harbour the insertion or deletion plasmids are propagated and the plasmids are isolated from the cells in a known manner and subjected to further purification. The purification is effected, for example, by means of isopycnic centrifugation in a density gradient of, for example, CsCl or by means of affinity purification on commercially obtainable silica particles.

3. Transfection:
Purified circular or linearized plasmid DNA is preferably used for the transfection. The purification is effected as indicated under section 2 (above), for example.

4. Culturing transfected and infected cells
The cells are cultured using the above-described methods. When a cytopathic effect appears, the culture medium is removed, where appropriate freed from cell debris by centrifugation or filtration and, where appropriate stored, and also worked up using the conventional methods for the single-plaque purification of viruses.

The following method is employed when preparing recombinant PPV:

BK-KL-3A cells which have grown to confluence are infected with an infection dose having an MOI (multiplicity of infection) of from 0.001 to 5, preferably of 0.1. Two hours later, the infected cells are transfected, for example, with the DNA (2–10 $\mu$g) of the plasmid pMT-10, either using the $CaPO_4$-glycyerol shock method or using a Transfection Kit in accordance with the manufacturer's instructions (DOSPER, Boehringer-Mannheim). These cell cultures are then incubated with medium at 37° C. and under a 5% $CO_2$ atmosphere for from three to six days until a cpe or plaque formation becomes visible.

Depending on the inserted foreign DNA, recombinant PPV are identified by:

a. detecting the foreign DNA, e.g. by means of DNA/DNA hybridizations
b. amplifying the foreign DNA by means of PCR
c. expressing the foreign DNA with the aid of recombinant viruses With regard to a.

For this, the DNA is isolated from the virus in question and hybridized with nucleic acid which is at least in parts identical to the inserted foreign DNA.

The PPV which have been single-plaque purified and which have been identified as recombinant are preferably tested once again for the presence and/or expression of the foreign DNA. Recombinant PPV which stably contain and/or express the foreign DNA are available for further use.

With regard to c.

Expression of the foreign DNA can be detected at the protein level by, for example, infecting cells with a virus and then carrying out an immunofluorescence analysis using specific antibodies against the protein encoded by the foreign DNA, or by carrying out an immunoprecipitation or a Western blotting using antibodies against the protein encoded by the foreign DNA using the lysates of infected cells.

Expression of the foreign DNA can be detected at the RNA level by identifying specific transcripts. For this, RNA is isolated from Virus-infected cells and hybridized with a DNA probe which is at least in parts identical to the inserted foreign DNA.

EXAMPLES

The following examples describe a region of the PPV genome which is suitable for the insertion and expression of homologous and heterologous genes, or parts thereof. Suitable genomic fragments are contained in HindIII fragment I of PPV ovis strain D1701 (and its respective derivatives) (sequence listing ID No: 8 and ID No: 12).

1. Cloning HindIII Fragment I

After purified viral DNA had been cleaved with the restriction enzyme HindIII, the resulting DNA fragments were separated by agarose gel electrophoresis and fragment I, which is approximately 5.6 kbp in size, was excised and isolated and purified using the Qiaex® method (Qiagen). Standard techniques (Maniatis et al.) were used to clone this DNA fragment into the vector plasmid pSPT18 (Boehringer, Mannheim), which had been cleaved with HindIII and treated with CIP (calf intestinal phosphatase). The resulting recombinant plasmids, pORF-1 and pORF-2, only differ in the orientation of the insert. The construction of a restriction map made it possible to carry out further subcloning, as shown in FIG. 1. Southern blot hybridization was used to test all the recombinant plasmid DNAs for restriction enzyme-digested viral or plasmid DNA in order to check their identity and viral origin.

2. DNA Sequencing

The DNA sequencing was effected by using the double-stranded DNA of the different recombinant plasmids and SP6-specific and T7-specific primers which bind to the two ends of the cloning site of the vector plasmid pSPT18. Sanger's dideoxy chain termination method was carried out in the presence of $^{35}S$-[$\alpha$]-dATP and T7-DNA polymerase in accordance with the manufacturer's (Pharmacia-Biotech) recommendations. A large number of oligonucleotides were synthesized in keeping with the DNA sequence which was obtained and then used for sequencing both strands of the HindIII fragment I. 7-Deaza-GTP was used to resolve sequencing artefacts or band compressions due to the relatively high G+C content of the viral DNA insert (64.78%) and the sequencing products were, if necessary, separated in formamide-containing denaturing polyacrylamide gels.

3. Identifying Potential Genes

A computer-assisted analysis of the resulting DNA sequence (sequencing listing ID No: 8 and ID No: 12) disclosed several possible open reading frames (ORFs). The amino acid sequences derived from these ORFs were used for gene homology searches (e.g. GCG program). Significant amino acid homologies with the following genes were detected as a result (see FIG. 1 as well).

3.1 An ORF was found which had amino acid homology (36.1 to 38.3% identity; 52.8 to 58.6% similarity) with vascular endothelial growth factor (VEGF) of different mammalian species (e.g. mouse, rat, guinea pig, cow and man) and also with the VEGF gene homologue which was recently described in PPV strains NZ-2 and NZ-7 (Lit. #6). Other poxviruses, such as various orthopoxviruses, are not known to have a corresponding gene homology. This ORF, which is termed VEGF, encompasses 399 nucleotides and encodes a polypeptide which contains 132 amino acids and which has a calculated molecular weight of 14.77 kDa. Transcription analyses on total or oligo(dt)-selected RNA using Northern blot hybridization, RNA protection experiments and primer extension tests verified that the VEGF was expressed as an early gene from about 2 hours after the infection (p.i.) onwards. It was found that the specific mRNA covers from 422 to 425 bases, beginning directly downstream of a sequence which exhibits 100% homology with the critical region of a consensus motif which is typical for promoters of early vaccinia virus genes. The 3' end of the VEGF mRNA was mapped in a consensus sequence which is possessed in common by early transcripts of, for example, vaccinia virus genes. The size of this mRNA was estimated by Northern blot hybridization to be about 500 bases, which points to a poly(A) segment having a length of about 100 bases.

3.2 Another ORF was found which encodes a potential protein kinase (PK) having homology with a corresponding gene which is present in several orthopoxviruses (e.g. vaccinia virus, variola virus or Shope-fibroma virus) and is known as F10L. This gene homologue is transcribed late in the infection cycle of PPV strain D1701 (from 12 to 16 hours p.i.). The transcription start point is located a short distance downstream of a region which exhibits a high degree of homology with known promoters of late vaccinia virus genes.

3.3 Other possible ORFs were found which to date do not exhibit any conspicuous homologies with known gene sequences. Of particular interest is a potential gene which is termed gene HD1R (FIG. 1). Analyses such as those described, above demonstrated the transcription of a specific early mRNA having a size of approx. 1.6 kb.

3.4 Finally, an ORF which overlaps the 3' end of F10L and the 5' end of VEGF was found by computer (F9L, FIG. 1). Sequence comparison showed homology with the vaccinia virus F9L gene.

3.5 By comparing with known DNA sequences of the orf strains NZ-2 and NZ-7, it was possible to fix the beginning of the so-called ITR region in the D1701 genome at nucleotide position 1611 of HindIII fragment I. The ITR region is a sequence region which appears at the end of the poxvirus genome and which is likewise present, in the reverse orientation, at the other end of the genome and is therefore termed an inverted repeat region (ITR) (see sequence listing ID No: 4). The sequence comparison finding tallies with experiments on the localization in the genome of the D1701 HindIII fragment I cloned into pORF-1. The map of this fragment, and of the presumably identical HindIII fragment H, is depicted in FIG. 2. From this, it can be concluded that the D1701 genome ITR encompasses approx. 2.6 kbp. Experiments to determine the 3' end of the D1701 VEGF mRNA revealed that at least one further virus-specific RNA starts in the ITR between approx. 40 and 220 bp after the transition to the ITR. Because of amino acid homology with NZ-2, the corresponding gene was termed ORF3 (FIG. 1). Prior to the putative 5' end of the ORF3 mRNA, there is a consensus sequence which is typical for an early poxvirus promoter. It has not so far been possible to find homology with other genes.

4. Introduction of DNA Sequences into HindIII Fragment I

The possibility was studied of using the described HindIII DNA fragment (cloned in plasmids pORF-1 and pORF-2) for introducing homologous or heterologous DNA sequences. In that which follows, three different strategies were used to achieve this goal.

Plasmid pGSRZ, which contains the functional LacZ gene from *E. coli* under the control of the 11K vaccinia virus promoter, was constructed for the following examples. To this end, the relevant parts of the DNA of plasmid pUCIILZ (see Lit. #7) were isolated and cloned into plasmid pSPT18. This functional 11K/LacZ gene combination (termed LacZ cassette below) can be obtained by isolating a 3.2 kb SmaI/SalI fragment from pGSRZ (FIG. 3).

Construction of the Selection Cassettes

Various so-called selection cassettes were constructed using the plasmids pGSSRZ (contain the LacZ gene under the control of the vaccinia virus promoter $P_{11K}$), pMT-1 (contain the PPV VEGF promoter) and pMT5 (contain the *E. coli* gpt gene), as depicted in FIG. 7. Synthetic complementary oligonucleotides which represented the sequence of the VEGF promoter ($P_{VEGF}$) were prepared and inserted into the SmaI cleavage site of pSPT18 (pMT-1). The plasmids pMT-2 and pMT-4 were then prepared by removing the LacZ gene from p18Z (obtained by inserting the BamHI fragment from pGSRZ into pSPT18), or the gpt gene from pMT-5, respectively, by means of BamHI cleavage and then inserting them into pMT-1 (FIG. 7).

The functional gpt gene was amplified from the GPT plasmid pMSG (Pharmacia-Biotech) by means of PCR and then cloned into the vector pCRII by means of so-called TA cloning in accordance with the manufacturer's (Invitrogen Inc.) instructions.

It was subsequently possible, as depicted diagrammatically in FIG. 7, to construct double selection cassettes which express the LacZ gene, or the gpt gene, respectively, under the control of the 11K promoter and/or the $P_{VEGF}$ in the combinations and orientations shown.

In accordance with Example 4.3.1 (LacZ-VEGF deletion) or 4.3.2 (intergenic-Bal31), these selection cassettes can be inserted, after appropriate restriction enzyme cleavage and isolation, into the different PPV orf DNA plasmids. The plasmid pMT-10 was constructed after inserting a double selection cassette into the described plasmid pdV-500, which exhibits a 312 bp deletion of the PPV D1701 VEGF gene. By means of this construction, the functional lacZ and gpt genes were inserted in place of the VEG ORF which was removed by the deletion. After transient expression tests, it was possible to demonstrate the activity of the LacZ gene in PPV D1701-infected cells (not shown) so that a selection was subsequently carried out for VEGF deletion mutants of D1701 which were expressing gpt and lacZ.

4.1 Insertion into Intergenic, Non-coding Regions

Identification or creation of new unique restriction sites which are located in an intergenic, non-coding part. These sites are then used for inserting foreign DNA sequences which encode functional and detectable gene products (e.g. the *E. coli* LacZ gene) or parts thereof.

Example 4.1.1

The plasmid pORF-PB (FIG. 1) contains a single NruI cleavage site, which is located between the protein kinase (F10L) and the HD1R gene. After pORF-PB had been linearized with this restriction enzyme, the LacZ cassette was ligated (after a filling-in reaction) to it by means of blunt-end ligation. Recombinant plasmids which contain the functional LacZ gene were selected after cleavage, e.g. with BglI, and the correct insertion was demonstrated by means of Southern blot hybridization using a LacZ-specific probe and by means of partially sequencing the LacZ/PPV DNA transition.

Example 4.1.2

The same approach as described in the above example was used downstream of the VEGF gene (cleavage at the BstEII site, FIG. 1) and in the potential gene ORF 3 in the ITR region (partial degradation with XbaI in order to prevent cleavage of the XbaI site in the pSPT18 cloning site).

Example 4.1.3

The technique of PCR mutagenesis can be used to introduce a new, unique restriction site at any desired point in cloned PPV DNA fragments (see FIG. 5, Lit. #12). To this end, two PCR reactions are carried out separately, using the primer pairs E1+EV2 (PCR A) and EV1+XB (PCR B), respectively. All the primers cover 25 nucleotides which are identical to the PPV DNA sequence at the given sequence positions. Whereas primer XB constitutes the authentic sequence, for example around the XbaI site (FIG. 1), a new EcoRI site was introduced into the 5' end of primer E1 and a new EcoRV site was introduced into primers EV1 and EV2 (which are complementary to each other). The EcoRV site, which is not originally present in the entire sequence of pORF-1 or pORF-2, was inserted at the point which was chosen for introducing the LacZ cassette. The PCR products which are obtained from reactions A and B are purified, denatured into single strands and mixed together under reassociation conditions; they are then used for the last PCR reaction; i.e. PCR C. E1 and XB are now used as primers in order, in this example, to extend the left 793 bp of pORF-1. After gel isolation and purification, the PCR product resulting from reaction C is cleaved with EcoRI and XbaI and then ligated to plasmid pORF-XB, which has been cleaved with EcoRI and XbaI. As a result, plasmid pORF-1EV (FIG. 5) contains the EcoRV restriction site at the desired position; it can then be used for being linearized and ligated to the LacZ cassette.

In addition, mispairing primers, which contain defined base changes or a deletion of a single base, can be used for the method described in this example in order to produce, for example, translation stop codons or amino acid deletions at any desired point in the viral DNA sequence.

4.2 Intragenic Insertion without Deletion of ORF Sequences

New or additional sequences can be introduced into the coding sequences of one of the described ORFs after cleaving at restriction sites which only occur once in the selected gene.

Example 4.2.1.

The unique XcmI site, which is located in the right-hand part of the F10L gene homologue, was used to linearize plasmid pORF-1. Both the LacZ cassette and the cleaved pORF-1 DNA were provided with blunt ends using T4 DNA polymerase or Klenow DNA polymerase and then ligated; competent *E. coli* bacteria (DHαF') were then used for the transformation. The resulting bacterial colonies were tested for positive recombinant plasmids by means of colony filter hybridization using a LacZ-specific probe, and the corresponding plasmid DNAs were cleaved with restriction enzymes.

Example 4.2.2

The VEGF-encoding region contains a single Styl site, which was used for inserting the LacZ cassette, as described above.

4.3 Deletion of Viral Sequences

The following examples describe the removal of both coding (intragenic deletions) and non-coding (intergenic deletions) regions:

Example 4.3.1

Restriction enzymes are used to remove defined parts of the HindIII DNA fragment I in order to replace the deleted viral sequences by inserting foreign genes or parts of these genes. This was effected by cleaving plasmid pORF-PA with the restriction enzyme NruI (at a point in the ITR region, FIG. 1), as a result of which a 396 bp fragment was deleted. After a filling-in reaction, the LacZ cassette was ligated as described above. FIG. 3 shows diagrammatically the deletion of the 396 bp fragment from pORF-PA and the insertion of the LacZ cassette. FIGS. 3 and 4 show the deletion/insertion plasmids pCE4 and pCE9 which were constructed in this way and which derive from pORF-PA.

Example 4.3.2

Individual restriction sites in the HindIII DNA fragment were used as starting points for effecting a bidirectional deletion of sequences under the influence of the endonuclease Bal31, as is outlined diagrammatically in FIG. 6. The enzymes StyI and XcmI were used for the restriction degradation, in the case of plasmid pORF-PA and of plasmid pORF-1 or pORF-XB, respectively, in order to open the genes which encode VEGF and protein kinase F10L, respectively (FIG. 1 and 6). After the exonuclease Bal31 had been added, aliquots were removed from the reaction every 2 minutes and the reaction then stopped. Cleavage of the timed samples with, for example, the restriction enzyme BglI, and subsequent gel electrophoresis, made it possible to estimate the size of the DNA segment deleted by the Bal31. Mixtures of the suitable timepoint samples were then used to close the DNA ends by means of a filling-in reaction. Two complementary oligonucleotides constituting new unique SmaI, SalI and EcoRV restriction sites were then hybridized and the resulting double-stranded primer molecules (termed EcoRV linkers) were ligated to the blunt-ended Bal31 products. After having transformed bacteria, plasmid DNA was isolated and cleaved with EcoRV, which does not possess any recognition site in the DNA sequence of the PPV HindIII fragment I. Every plasmid DNA having an EcoRV site therefore contained the inserted linker sequence and was then used for ligating the blunt-ended LacZ cassette into the new EcoRV site. It was possible to determine the precise size of the DNA deletion produced in each resulting recombinant plasmid DNA by means of sequencing using the single-stranded EcoRV linkers and using suitable LacZ gene-specific primers.

5. Detection and Identification of the VEGF Gene in Other Parapoxviruses

Knowledge of the DNA region which encodes VEGF in D1701 makes it possible to prepare specific DNA probes and PCR primers for identifying this gene in other parapoxvirus strains which may have widely differing restriction profiles. The following possibilities were tested to this end: (i) isolating a TaqI subfragment (366 bp) of pORF-PA as a hybridization probe representing the central part of the D1701 VEGF gene; (ii) amplifying the complete VEGF ORF using suitable synthetic primers and then cloning the PCR product into plasmids; (iii) primers which cover different parts of the VEGF gene were used for PCRs in the presence of PPV DNAs as templates, and also as specific hybridization probes.

After having been labelled radioactively, these probes were used successfully for Southern and dot/spot blot hybridization with the genomic DNA of various isolates and strains of Parapox ovis, Parapox bovis 1 (bovine papular stomatitis; BPS) and Parapox bovis 2 (milker's nodule). The Southern blot hybridization showed VEGF-positive signals with defined PPV DNA fragments which make it possible to map the VEGF genes of the various PPVs in further detail.

In addition, the same probes can be used for comparative RNA analyses, such as Northern blot hybridization, in order to test expression of potential VEGF genes in other PPV strains.

6. Production of D1701 Recombinants

BK-KL-3A cells which are grown to confluence were infected with an infection dose having an moi (multiplicity of infection) of 0.1. Two hours later, the infected cells were transfected with, for example, DNA (from 2 to 10 μg) of the plasmid pMT-10 either by means of the CaPO$_4$-glycerol shock method or using a transfection kit (DOSPER, Boehringer-Mannhein) in accordance with the manufacturer's instructions. These cell cultures were then incubated with selective medium (HAT medium+MPA mycophenol acid–xanthine–5% FCS) at 37° C. for from three to six days and under a 5% CO$_2$ atmosphere until cpe or plaque formation became visible. Depending on the degree of the virus-induced cpe:

(a) The cell lysate was obtained, a dilution series was prepared and a plaque test was carried out on BK-KL-3A cells. The agarose medium mixture which was added contained 0.3 mg/ml Bluo-Gal (GIBCO-BRL Life Sciences) in order to identify blue plaques which contained the LacZ-expressing, MPA-resistant D1701 recombinants.

(b) After individual plaques had formed, the agarose/Bluo Gal mixture described in (a) was added and blue individual plaques were picked.

The viruses obtained in (a) or (b) are employed, as described below, for infecting BK-KL-3A and subjected to at least two further plaque titrations and purifications until a 100% homogeneous recombinant virus population has been obtained.

7. VEGF Promoter

As outlined in Chapter 3.1, the VEGF gene of D1701 is an early gene; the specific mRNA is transcribed in large quantities in D1701 virus-infected cells from two to four hours after the infection up to relatively late times in the infection. For this reason, the D1701 VEGF promoter region which has been identified should be very useful for controlling the expression of foreign genes, or parts of these genes, in recombinant PPV viruses. The sequence which encompasses the VEGF promoter (35 to 40 nucleotides; sequence listing ID No: 6) can be isolated by means of (i) PCR using the appropriate primers which flank the promoter region, (ii) subcloning the appropriate DNA fragments, or (iii) synthesizing the promoter sequence as an oligonucleotide.

After the VEGF promoter has been linked to any gene of interest or DNA sequence, the resulting gene cassette can be used for preparing recombinant PPV in accordance with any method described in the preceding chapters.

8. 10 kDa Gene

A specific PCR for detecting the PPV 10 kDa gene was established on the basis of the published DNA sequence of the 10 kDa gene from the PPV strain NZ-2 (Lit. #8). After having carried out a PCR using the synthetically prepared primers 10K-up (5-CAATATGGATGAAAATGACGG-3) and 10 k-down (5-CAGACGGCAACACAGCG-3), success was achieved in amplifying a specific product of 297 base pairs in size. Subsequent cloning (TA cloning kit, Invitrogen Inc.) resulted in plasmid pJS-1, which contained the 297 bp PCR product as an EcoRI fragment. DNA sequencing of the two DNA strands of the pJS-1 insertion demonstrated that the 10 kDa-specific sequence was present. According to this sequence, D1701 encodes a 91-amino acid 10 kDa protein which possesses 93.3% amino acid identity and 96.7% amino acid similarity with the NZ-2 PPV strain.

Southern blot hybridization using radioactively labelled pJS-1 was employed to locate the 10 kDa gene in EcoRI fragment E (4.25 kbp) of the D1701 genome. Accordingly, this gene, as in the case of NZ-2, is located in the right-hand part of the viral genome and contains the cleavage site of HindIII fragments K and G (FIG. 2).

Plasmids pDE-E1 and pRZ-E1, which contain the 4.25 kbp D1701 EcoRI fragment E, are used for preparing plasmids in which the 10 kDa gene contains insertions or deletions (in principle as previously described). The HindIII cleavage site (fragments K-G) in the N-terminal segment of the D 1701 10 kDa gene (#124–#129) sequence ID No: 11) can be used both for directly inserting foreign DNA and for deleting (see bidirectional digestion with Bal31) the 10 kDa gene. For the latter construct, the second HindIII cleavage site (the multiple cloning site of vector plasmid pSPT18) was removed from plasmid pDE-E1. For this, pSPT18 DNA was cleaved with HindIII, after which the HindIII cleavage site was destroyed by treating with Klenow and the plasmid was religated. The 4.25 kbp D1701 EcoRI fragment E was then cloned into the EcoRI restriction site of this new vector plasmid pSPT18dH. The resulting plasmid, pRZ-E1 (FIG. 8), now possesses a unique HindIII cleavage site in the 10 kDa gene, with this site permitting further simple manipulations.

Southern blot hybridization using pDE-E1 and pJS-1 as radioactively labelled probes, and also PCR investigations, demonstrate that the genomes of different PPV bovis 1 strains do not contain any 10 kDa-specific sequences. This indicates that the 10 kDa PPV gene is not essential (Büttner M. et al. 1996, Lit. #10).

REFERENCE LIST

1. Robinson, A. J. and Lyttle, D. J. 1992. Parapoxviruses: Their biology and potential as recombinant vaccines. In: Recombinant poxviruses edts. M. M. Binns and G. L. Smith, CRC Press Inc.
2. Mayr, A. 1990. Chapter 7 (Ecthyma (Orf) Virus) in: Virus Infections of Vertebrates, Vol. 3: Virus Infections of Ruminants, 1990, Elsevier Science Publishers B.V., The Netherlands.
3. Mazur, C., Rangel Filho, F. B. and Galler, R. 1991. Molecular analysis of contagious pustular dermatitis virus: A simplified method for viral DNA extraction form scrab material. J. Virol. Methods 35, 265–272.
4. Mercer, A. A. 1994. 10th Int. Conf. on Poxviruses and Iridoviruses Apr. 30–May 5, 1994. Proceedings.
5. Fleming, S. B., Lyttle, D. J., Sullivan, J. T., Mercer, A. A. and Robinson, A. J. 1995. Genomic analysis of a transposition-deletion variant of orf virus reveals a 3.3 kbp region of non-essential DNA. J. gen. Virol. 76, 2669–2678.
6. Lyttle, D. J., Fraser, K. M., Fleming, S. B., Mercer, A. A. and Robinson, A. J. 1994. Homologues of vascular endothelial growth factor are encoded by the poxvirus orf virus. J. Virol. 72, 1171–1181.
7. Sutter, G. and Moss, B. 1992. Nonreplicating vaccinia vector efficiently expresses recombinant genes. Proc. Natl. Acad. Sci. USA 89, 10847–10851.
8. Naase, M., Nicholson, B. H., Fraser, K. M., Mercer, A. A. and Robinson, A. J. 1991. An orf virus sequence showing homology to the 14K fusion protein of vaccinia virus. J. gen. Virol. 72, 1177–1181.
9. Graham, F. L. and van der Eb, A. J. 1973. A new technique for the assay of infectivity of human adenovirus 5 DNA. Virology 52, 456–467.
10. Büttner, M., McInnes, C., von Einem, C., Rziha, H. J. and Haig, D. 1996. Molecular discrimination of parapoxviruses from different species. 11th Poxvirus and Iridovirus meeting, May 4–9, Toledo, Spain.
11. Sambrock, J., Frisch, E. F. and Maniatis, T. 1989. Molecular Cloning, A laboratory manual, 2nd edition. Cold Spring Harbor Laboratory Press.
12. Jacobs, L., Rziha, H.-J., Kimman, T. G., Gielkens, A. L. J. and von Oirschot, J. T. 1993. Deleting valine-125 and cysteine 126 in glycoprotein gl of pseudorabies virus strain NIA-3 decreases plaque size and reduces virulence for mice. Arch. Virol. 131, 251–264.
13. Virologische Arbeitsmethoden, [Practical Methods in Virology], 1989. Biochemische und Biophysikalische Methoden, [Biochemical and Biophysical Methods], VEB Fischer Verlag.
14. Sharp, P. A., Berk. A. J. and Berger, S. M. 1980. Transcription maps of adenovirus. Meth. Enzymol. 65, 750–768.
15. Watson, J. D., Hopkins, N. H., Roberts, J. W., Seitz, J. A. and Weiner, A. M. 1987. Molecular Biology of the Gene, Benjamin/Cummins Publishing Company, Menlo Park.
16. Faulkner, F. G. and Moss, B. 1988. *Escherichia coli* gpt gene provides dominant selection for vaccinia virus open reading frame expression vectors. J. Virol. 62, 1849–1854.
17. Boyle, D. B. and Coupar, B. E. 1988. Construction of recombinant fowlpox viruses as vectors for poultry vaccines. Virus Res. 10, 343–356.
18. Methods in Virology, Vol. VI, 1977. edts. Maramorosch, K. and Koprowski H. Academic Press. New York, San Francisco.
19. Hattori, M. and Sakaki Y. 1986. Dideoxy sequencing method using denaturated plasmid templates. Anal. Biochem. 152, 232–238.
20. Chomczynski, P. and Sacchi, N. 1987. Single step method of RNA isolation by acid guanidinium-thiocyanate-phenol-chloroform extraction. Ana. Biochem. 162, 156–159.

ID No: 1
Sequence ID No: 1 of the application shows the VEGF gene which is located on HindIII fragment I of strain PPV D1701.
Additional information:
Early promoter: Nucleotides 50 to 64
mRNA start: Nucleotides 78 or 80
mRNA stop: Nucleotides 498 to 500
Translation start: Nucleotides 92 to 94
Translation stop: Nucleotides 488 to 490

ID No: 2
Sequence ID No: 2 of the application shows the protein kinase gene F10L (version 1) which is located on HindIII fragment I of strain PPV D1701
Additional information:
Late promoter: Nucleotides 48 to 66
mRNA start: Nucleotides 74 to 78
Translation start: Nucleotides 94 to 96
Translation stop: Nucleotides 1738 to 1740

ID No: 3
Sequence ID No: 3 of the application shows the HD1R gene segment which is located on HindIII fragment I of strain PPV D1701.

ID No: 4
Sequence ID No: 4 of the application shows the ITR region which is located on HindIII fragment I of strain PPV D1701 and the ORF3 gene which is found in this region.
5 Additional information:
Beginning of ITR region: Nucleotide 7
Early promoter: Nucleotides 18 to 33
ORF3 mRNA start: Nucleotides 40 to 41
ORF3 mRNA stop: Nucleotides 673 to 679
ORF3 translation start: Nucleotides 111 to 113
ORF3 translation stop: Nucleotides 562 to 564

ID No: 5
Sequence ID No: 5 of the application shows the F9L gene homologue (version 1) which is located on HindIII fragment I of strain PPV D1701.
Additional information:
Start codon: Nucleotides 48 to 50
Stop codon: Nucleotides 861 to 863

ID No: 6
Sequence ID No: 6 of the application shows the VEGF promoter region which is located on HindIII fragment I of strain PPV D1701.

ID No: 7
Sequence ID No: 7 of the application shows the intergenic region which is situated between the HD1R and PKF10L genes and is located on HindIII fragment I of strain PPV D1701.
Putative HD1R translation stop: Nucleotides 25 to 27
PKF10L translation start: Nucleotides 223 to 225

ID No: 8
Sequence ID No: 8 of the application shows the complete nucleotide sequence of HindIII fragment I (version 1) of PPV strain D1701.

ID No: 9
Sequence ID No: 9 of the application shows version 2 of the protein kinase F10L gene which is located on HindIII fragment I of strain PPV D1701.
Additional information:
Late promoter: Nucleotides 48 to 66
RNA start signal: Nucleotides 72 to 80
mRNA start: Nucleotides 74 to 78
Translation start: Nucleotides 94 to 96
Translation stop: Nucleotides 1585 to 1588

ID No: 10
Sequence ID No: 10 of the application shows version 2 of the F9L gene homologue which is located on HindIII fragment I of strain PPV D1701.
Additional information:
Translation start: Nucleotides 50 to 52
Translation stop: Nucleotides 722 to 724

ID No: 11
Sequence ID No: 11 of the application shows the 10 kDa gene which is located on EcoRI fragment E of strain PPV D1701.
Additional information:
Translation start: Nucleotides 5 to 7
Translation stop: Nucleotides 275 to 277

ID No: 12
Sequence ID No: 12 of the application shows the complete nucleotide sequence of version 2 of HindIII fragment I of PPV strain D1701.

ID No: 13
Sequence ID No: 13 of the application shows version 3 of the protein kinase F10L gene which is located on HindIII fragment I of strain PPV D1701.
Additional information:
Late promoter: Nucleotides 48 to 66
RNA start signal: Nucleotides 72 to 80
mRNA start: Nucleotides 74 to 78
Translation start: Nucleotides 94 to 96
Translation stop: Nucleotides 1585 to 1588

ID No: 14
Sequence ID No: 14 shows the amino acid sequence of the PPV D1701 protein kinase F10L homologue (deduced from sequence ID No: 13).

ID No: 15

Sequence ID No: 15 shows the amino acid sequence of the PPV D1701 VEGF homologue (deduced from sequence ID No: 1).

ID No: 16

Sequence ID No: 16 shows the amino acid sequence of the PPV D1701 F9L homologue (deduced from sequence ID No: 10).

LIST OF FIGURE

Figure 2:
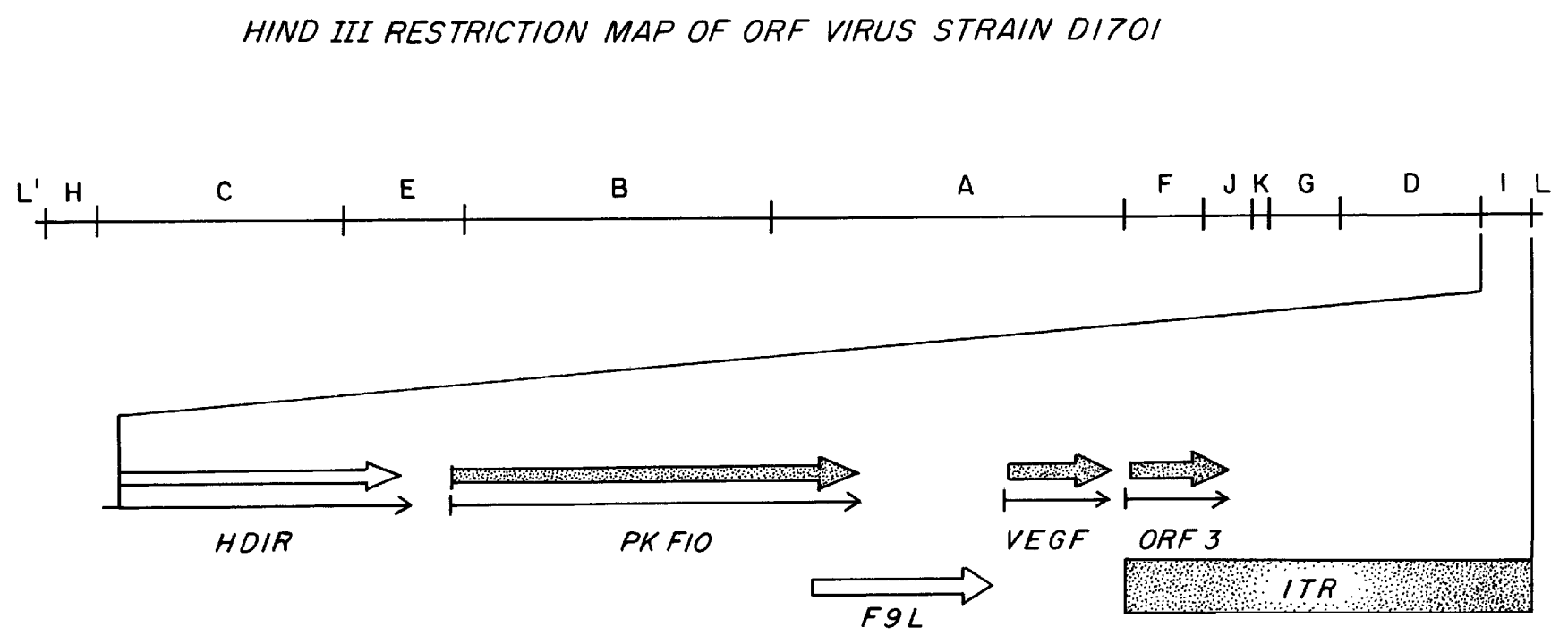

FIG. 2 shows the physical map of the HindIII recognition sites on the D1701 genome and the genes identified on HindIII fragment I, and also a part of the inverted terminal repeat region.

FIG. 4 shows plasmid pCE9 into which the LacZ cassette was inserted after linearizing by cleavage with XcmI.

FIG. 5 shows diagrammatically, as described in the text, the strategy for using PCR to generate new unique cleavage sites.

$P_{11K}$: vaccinia 11k promoter $P_{VEGF}$: PPV VEGF promoter

Sm: Sma I

B: BamHl

Figure 1:
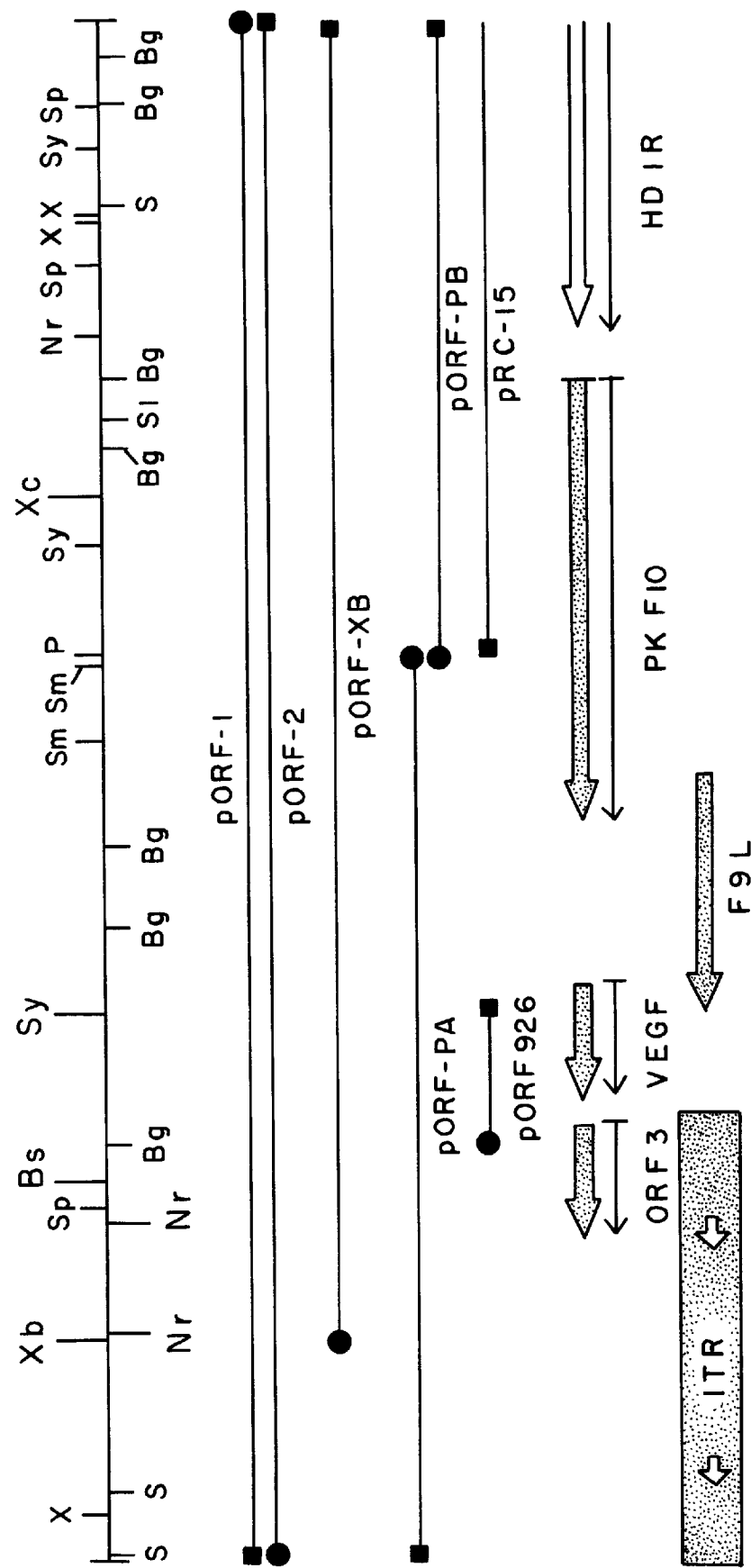
FIG. 1 shows the physical map of the orf D1701 HindIII fragment I in plasmids pORF-1/-2. The thin arrows indicate the identified mRNAs, while the thick arrows indicate the ORFs.
Figure 3:
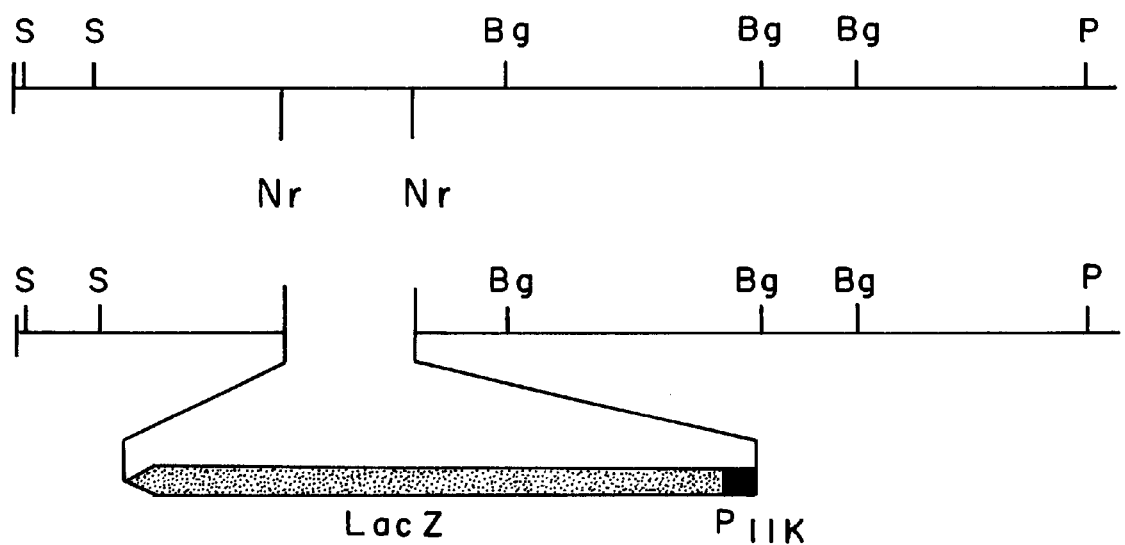
FIG. 3 shows plasmid pCE4. Following cleavage with NruI, a 396 bp fragment was replaced with the LacZ cassette.
Figure 6:
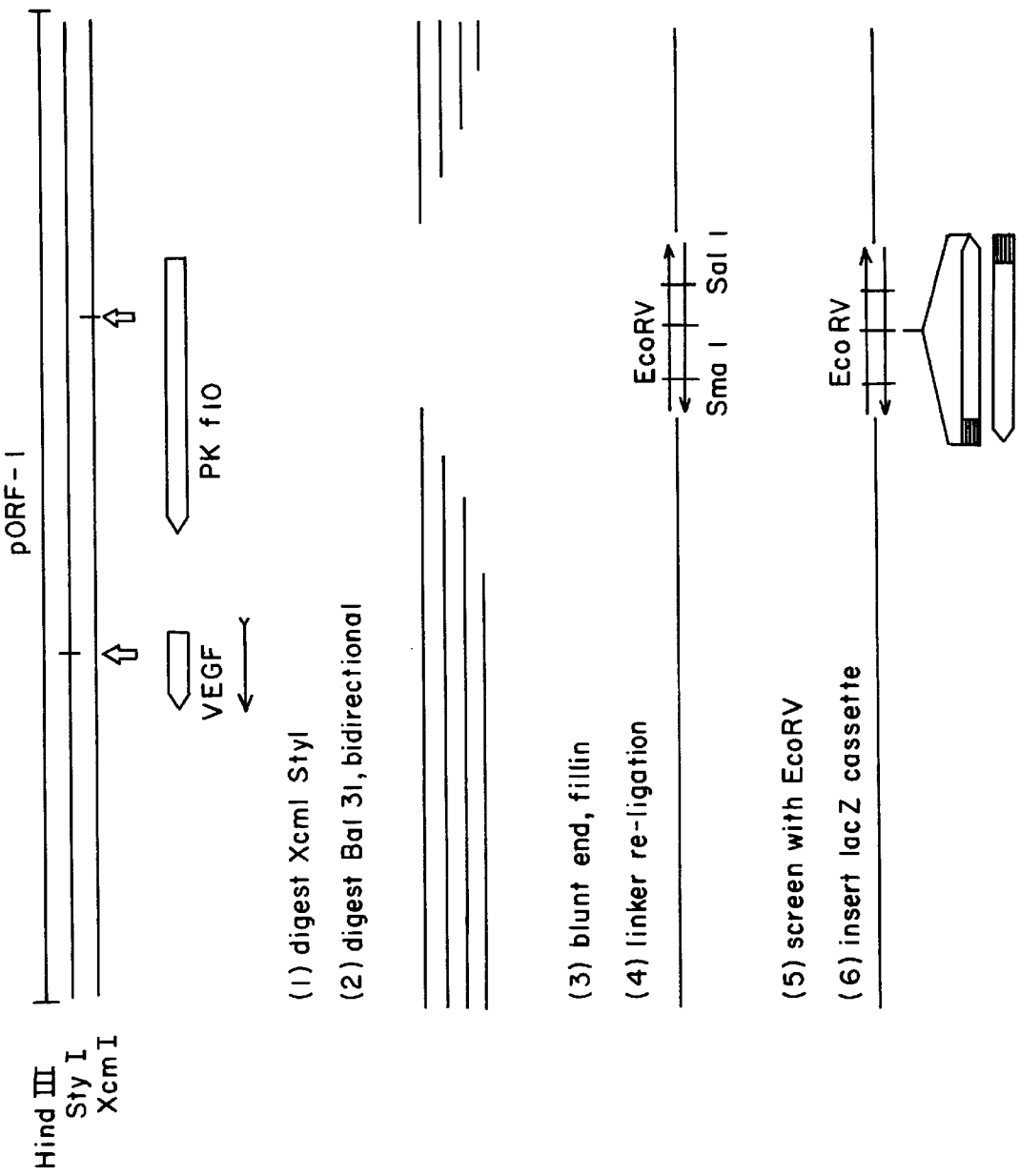
FIG. 6 shows diagrammatically the bidirectional truncation using nuclease Bal31 with subsequent insertion of the EcoRV linkers and the LacZ cassette.
Figure 7:
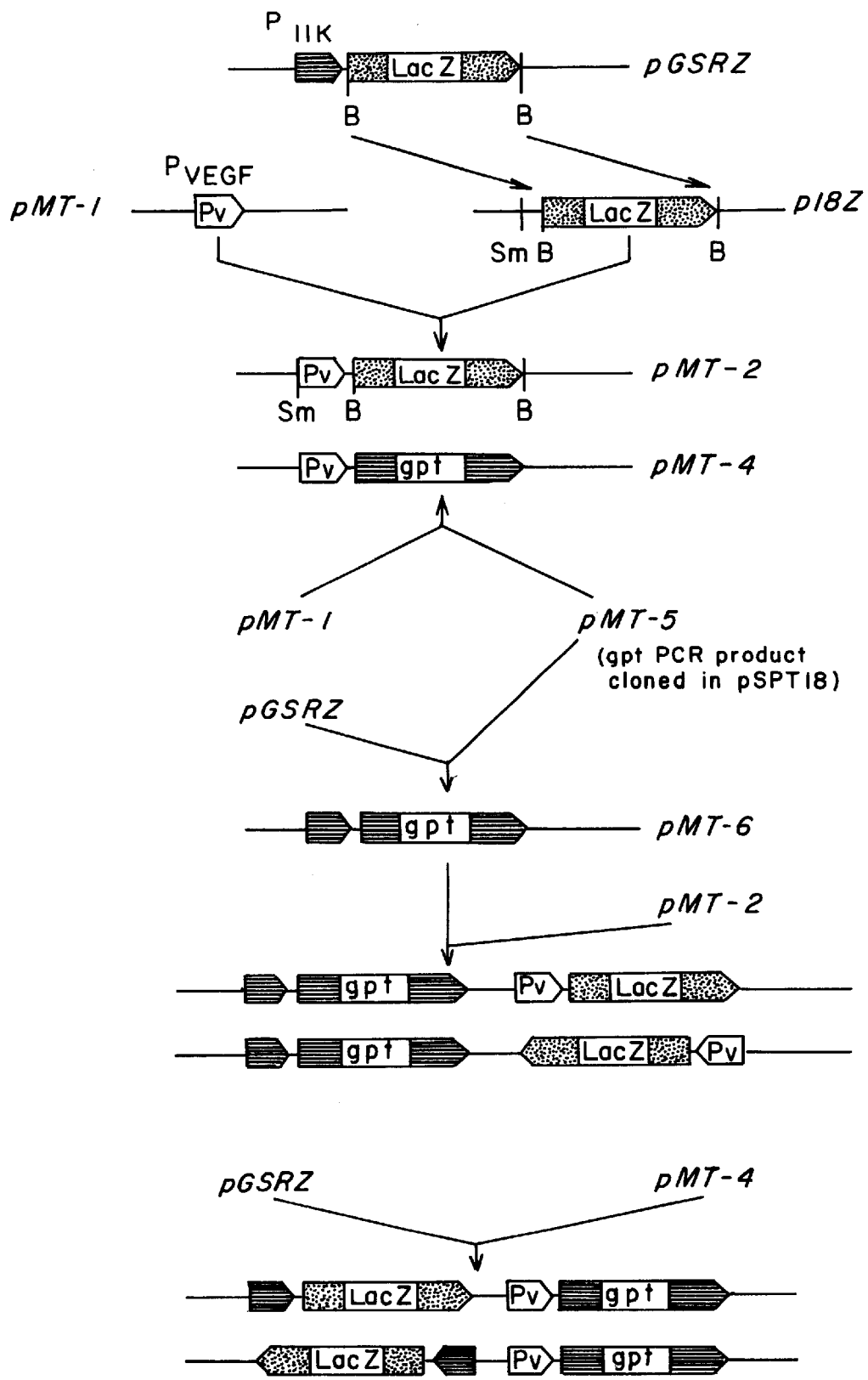
FIG. 7 shows the strategy for preparing the LacZ/gpt selection cassette.
Figure 8:
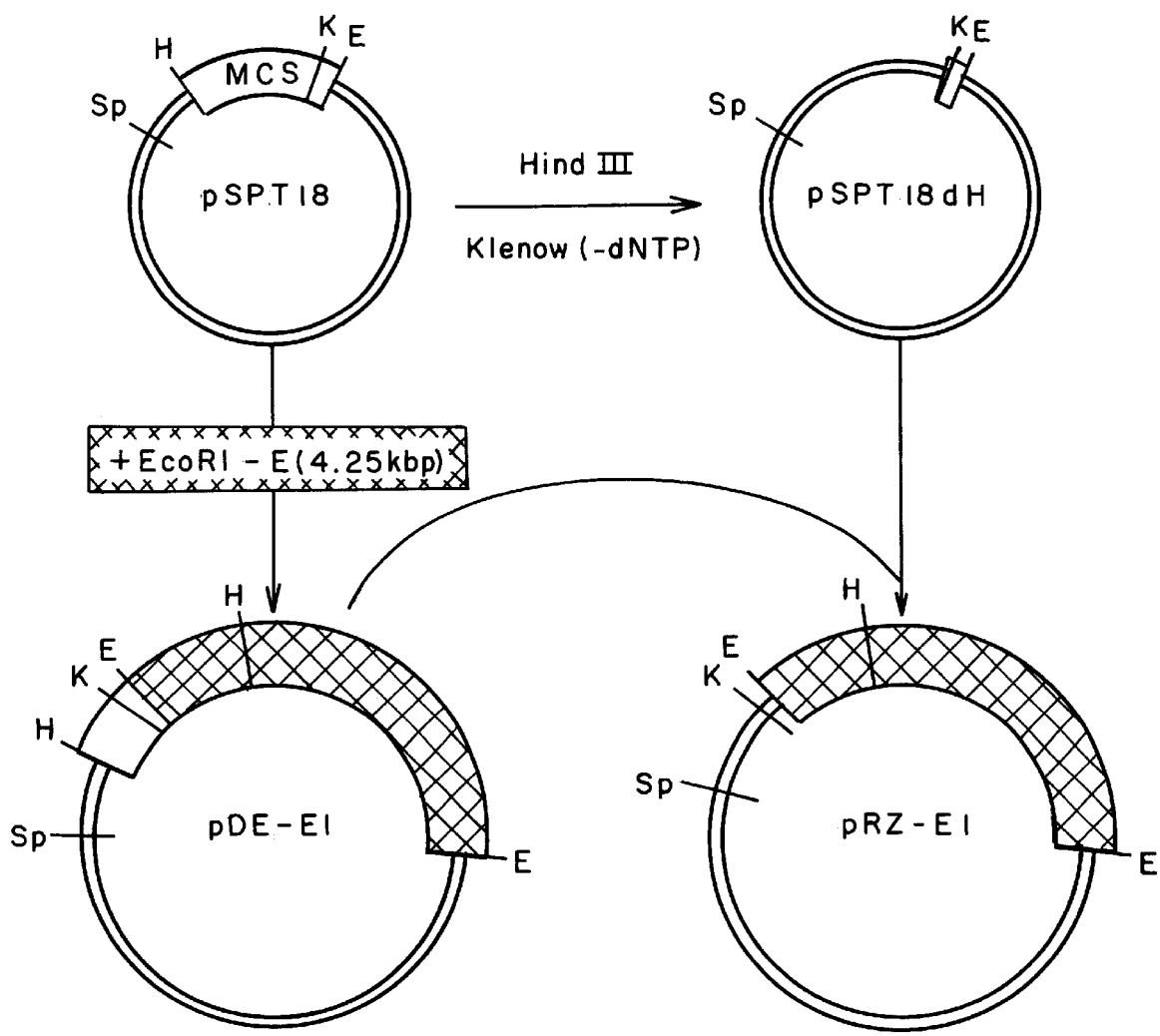

FIG. 8 shows diagrammatically the strategy for cloning PPV D1701 EcoRI fragment E, which contains the 10 kDa gene (as described in the text).

What is claimed is:

1. A recombinantly prepared parapoxvirus being derived from parapoxvirus strain D 1701 deposited under Reg. No. CNCM 1-751 and containing at least one insertion of a foreign DNA element within the Hind III fragment I of parapoxvirus strain D 1701, said Hind III fragment I having a size of about 5.6 kbp.

2. The recombinantly prepared parapoxvirus according to claim 1 wherein the insertion is located within the VEGF coding sequence or adjacent non coding sequences, said VEGF coding sequence being characterized by nucleotides 92 to 487 of the sequence as set forth under SEQ ID NO: 1.

3. The recombinantly prepared parapoxvirus according to claim 1 wherein the insertion is located within the ITR coding sequence or adjacent non coding sequences, said ITR sequence being characterized by the sequence as set forth under SEQ ID NO: 4.

4. The recombinantly prepared parapoxvirus according to claim 1 wherein the insertion encodes an immunogenic constituent of a pathogen.

5. A method of preparing a vaccine comprising incorporating the recombinantly prepared parapoxvirus according to claim 4.

6. Recombinantly prepared PPVs which contain insertions and/or deletions in the location of PK gene sequence or the adjacent non coding sequence.

7. Recombinantly prepared PPVs which contain insertions and/or deletions in location of the HD1R gene sequence or adjacent non coding sequences.

8. Recombinantly prepared PPVs which contain insertions and/or deletions in the location of the F9L gene sequence or adjacent non coding sequences.

9. Recombinantly prepared PPVs which contain insertions and/or deletions in the location of the gene sequence which encodes the ITR or the adjacent non coding sequences.

10. Recombinantly prepared PPVs which contain insertions and/or deletions in the intergenic sequence between the HD1R gene and the PK gene.

* * * * *

SEQUENCE LISTING (1) GENERAL INFORMATION:

(iii) NUMBER OF SEQUENCES: 18

(2) INFORMATION FOR SEQ ID NO: 1:

(i) SEQUENCE CHARACTERISTICS:
        (A) LENGTH: 540 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Parapox ovis
        (B) STRAIN: D1701-VEGF-Gen (xi) SEQUENCE DESCRIPTION: SEQ ID NO: 1:

```
GGTGCGCTAC CAATTCGCGC GGCCGGCCGC GCTGCGCGCG TAGCCGCGCA AAATGTAAAT      60

TATAACGCCC AACTTTTAAG GGTGAGGCGC CATGAAGTTT CTCGTCGGCA TACTGGTAGC     120

TGTGTGCTTG CACCAGTATC TGCTGAACGC GGACAGCACG AAAACATGGT CCGAAGTGTT     180

TGAAAACAGC GGGTGCAAGC CAAGGCCGAT GGTCTTTCGA GTACACGACG AGCACCCGGA     240

GCTAACTTCT CAGCGGTTCA ACCCGCCGTG TGTCACGTTG ATGCGATGCG GCGGGTGCTG     300

CAACGACGAG AGCTTAGAAT GCGTCCCCAC GGAAGAGGCA AACGTAACGA TGCAACTCAT     360

GGGAGCGTCG GTCTCCGGTG GTAACGGGAT GCAACATCTG AGCTTCGTAG AGCATAAGAA     420

ATGCGATTGT AAACCACCAC TCACGACCAC GCCACCGACG ACCACAAGGC CGCCCAGAAG     480

ACGCCGCTAG AACTTTTTAT GGACCGCATA TCCAAACGAT GATGCGATCA GGTCATGCGG     540
```

(2) INFORMATION FOR SEQ ID NO: 2:

(i) SEQUENCE CHARACTERISTICS:
        (A) LENGTH: 1740 base pairs (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Parapox ovis
        (B) STRAIN: D1701- Proteinkinase-Gen(Version 1)

(xi) SEQUENCE DESCRIPTION: SEQ ID NO: 2:

```
CGAGTGACTG CCCATCCCGT TGCTGCGCGA CTCGGGACTG CCCTCTGTTT TTCTTTCCCG     60
TTTCTTCTTA TTAGGTAGTT GTTGCCCACC TCCATGATCC TCGCACGCGC TGGCGGGCGA    120
CCTCGCACGC CCGCGGCGGC CGCGGCGGCC GCCGAGGACG GCAAGAACAG TGATCGCCGG    180
AAGCGCAAGC GCAAGACGCC CAACTGCGAA GACGCCGACA ACTCCGACGA CGAGCTAGCG    240
CAGACGCCGT GCGACCGCGA GTGGCCGGAC TGTCGCGCGA GCTCGATCAC GAGCTCCGAC    300
TCGGTCTCTC TCGGCGACGA GATCTACTTG CGGTACGTAG CCTCGCAGGT GGACTTCGCG    360
CAGACCTGGG CCCCGCCGGT GCGGCTGCTG CGCTTCTTCG GGAACTTCTC GAAGGAAACG    420
CTCAGCCGCA TGTCGCGGCG CGGGTACGTG AACCGCTCCT ACTTCCAGAT GGCGCACGCG    480
CGCTTCTCGC CCACCAACGA CGACATGTAC CACATGGCCA CTGGCGGGTA CGGCATCGTG    540
TTCCGCTTCG ACCGCTACGT GGTCAAGTAC GTCTTCGAGC ACCGCAACGG CATGTCCGAG    600
ATGGACGCCT CTACGGAGTA CACGGTGCCG CGGTTCCTGC GCAATAACCT CAAGGGCGAC    660
GAGCGCGAGT TCGTGGTCTG CGCGCTGGCC ATGGGGCTGA ACTACCGGCT GGGCTTCCTG    720
CACTCGCTGT ACCGGCGCGT GCTGCACACG CTGCTGCTGC TCATGCGCGT GGAGGAAGGC    780
CAGCGGCCCT CGGTAGAGAT GGCCAAGAAG CCGCTGCTGC GCTGGTTCGA GGCGCGCAAG    840
GACAGCGAGT CCTTCGTGCG CCTGGTCTCG TACTTCTACC CCTCGGCCGT GCAGAGCAAC    900
GTGAACCTGA TCAACAACTT CCACCACCTG GTGCACTTCT TTGAGCACGA GAAGCGCGCG    960
CGGTACGTGT TCGACCGCGG GGCCGTGATC GTGTTCCCTC TGGCGCGCGG GTCCGCGGAC   1020
TCGATCTCGC CGGAGGCGGC GGCAGCGCTG GGCTTCGCGC CGCACTCGGA GTTCCTCAAG   1080
TTCGTGTTCC TGCAGATCGC GCTGCTGTAC CTGAAGATAT ACGAGCTCCC GGGCTGCACG   1140
AACTTCCTGC ACGTGGACCT GAAGCCCGAC AACGTGCTCA TCTTCGACAG CGCGCGCGCT   1200
CAGCGTGACT GCGGCCGGTG CGACTTTTCG CTTCGAAGAG CCCGTGCGCG CGGCGCTGAA   1260
CGACTTCGAC TTCGCGCGCG TGGCCACCAT CGAGAACCGC AAGATCGCGG GCAGCGTCCG   1320
CGTGCCGCAG AACTGGTACT ACGACTTCCA CTTCTTCGCG CACACGCTGC TGCGCGCGTA   1380
CCCGCACATC GCCGCGGAGG ACCCGGGCTT CCACGCGCTG CTCTCGGAGC TCACGGTCTC   1440
GTGCTCGCGC GGGACCTGCG ACCGCTTCCG GCTGCGCGTG TCCTCGCCGC ACCCCATCGA   1500
GCACCTCGCG CGGCTGGTGC GCCGCGACGT CTTCTCCCGC TGGATAAATG CCGCCGCGGA   1560
CGCCCCCGAC GCCGCACTCT CCTGAGCCCA CGCCCGCGGC GCCGGGCTCG CTGTACGACG   1620
TCTTCCTCGC GCGCTTCCTG CGCCAGCTGG CCGCGCGCGC GGCGCCGGCC TCGGCCGCCT   1680
GCGCCGTGCG CGTGGGTGCG GTGCGCGGCC GCCTGCGGAA CTGCGAGCTG GTGGTGCTGA   1740
```

(2) INFORMATION FOR SEQ ID NO: 3:

(i) SEQUENCE CHARACTERISTICS:
(A) LENGTH: 1080 base pairs (B) TYPE: nucleic acid
  (C) STRANDEDNESS: double
  (D) TOPOLOGY: linear (ii) MOLECULE TYPE: DNA (genomic)

(iii) HYPOTHETICAL: NO (vi) ORIGINAL SOURCE:
  (A) ORGANISM: Parapox ovis
  (B) STRAIN: D1701-HD1R-Genregion (xi) SEQUENCE DESCRIPTION: SEQ ID NO: 3:

```
AAGCTTGTTG CGCGAGTACG TGGTGACCCG CGCCTACTCG GATCAGACCG AGCCGATCAT     60

GGACTTGCTC ATCGGCATGG GCGCCGACGT GGACATGCAG GTCGGCGTGT GCCGCACGGC    120

GCTGCACGCC TGCCTTACGG GCTTGAACAC GAACCCGTGC ATGATTCGCG CGCTGCTTCG    180

GCGCGGCGCC AGCGTGACCG CAAAAGACAC CTACGAGATG ACGCCACTGG CGTGTTGCTG    240

AAGTCCGCGA GCGCGACGCC GGAGCTCGTG CGCATCCTCG TGGAAGCAGG CTCCGACGTG    300

AGCGCCACCG ACTTCCGCCT CAACGGCATG CTGCACCAGC ACGCAGTCCA CGCGCCCGCG    360

CGCGAGCGTC ATGCGCGAGC TCATCCGGCT GGGGTGCAGC CCAGCGGCCA AAAACATGTT    420

TGGGAACACG CCGATGCACA TGCTGGCCAT GGAAAGCTCC TGCCGCCGCT CGCTGATCCT    480

CCCGCTGCTG GAGGCAGGGC TTTCCGTGAA CGAGGAGAAC CTGCACTACG GCACCGTGCC    540

TCTGCACGTG GCCTCGGGGT ACGACAACAC GCAGGGCTGC CTCAAGCTCC TCCGGCAGGG    600

AGGAGACCCC ACCGTCGTGT CAGCCGCCGG ACGCACACCG ATCTCGAACA TGCTCGTCAA    660

AGCCAACCAC GTGGCGGTCG CCGGCGCGCT GTCGACGCAC CCGAGCGCGG CAGTGGTCGT    720

GCAGGCTCTC GAGCAGGCTC TCGAGAACGT GCTGAACGCC GGGCCCAGCG AGGCCTCGCG    780

GCTCGCCGTG GCCTTTGTGG TGGCGCGCGC CGGCGCATCC GCGCTACCGG AGGCCGTGCG    840

CCGTCTTCAC GAGGGCTTCG TCGCCGACTG CGAGCGCGAA GTCGCGTTGC TTTCCCGCAG    900

CATGCTCGGC ACACCGGCCG TGAGCGCGCT GGTCGTGCTG GTCAGCAAGG AGGTCTTTGG    960

CACTGTTATC TCCTCGCGTG CGCTGCGCGT CGCGCGGGAG GTCCGCGTGT ACGCAAGGCC   1020

GCTCCGCGAG GCGCTCATAA ATCTGCGCCA CAAATGCCGC TTAGTTTCCA GCCTTAAAAG   1080
```

(2) INFORMATION FOR SEQ ID NO: 4:

(i) SEQUENCE CHARACTERISTICS:
(A) LENGTH: 1616 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Parapox ovis
(B) STRAIN: D1701- ITR und ORF3 -Gen (xi) SEQUENCE DESCRIPTION: SEQ ID NO: 4:

```
AAGGAGGCTC CACGGAGCAA AGTGAAAAAG GACCGCCTAG AGTCGAGACC CCTCCCTCCC     60

GCCTCGGGCA AACCCACAGC CGCCGCAAAC ACCACACCCG CCGACCTACC ATGCACCCCT    120

CGCCGCGCCG GCTGCTCGGC GCGCTCGCGC TGCTGGCGCT GGGCTTCGCT CGGCGCGCTC    180

TTCGCCCCGC GGCGCCGCTC GTGCCGGCCG CCTTCCTGGA GGTGGGGCAC GTGCGCGCGA    240
```

-continued

```
ACCCGTCCGC CTCGGTGACC TGCCTCACGG TGGGCGGCGA CGGGCGGCAC ATGGCGGCGG    300

TCGCGCACGG CGGCGGGACG CTCTCGCCGG TGTACCCGCT GGCCGCCGGC ATGCACGCGA    360

CCTTCTCCTC CGCGCGCAAG GGCGCGCTGC TGCTGAACGT CGCGACCGTG ACTGTGTACG    420

ACGTGCGCGC GCTCGCCCCC GAGTTCGAGC TCGTCTGCAT CGCGGTGGTC GGCGGCTACA    480

ACTCGGCCGC GGCCGCCACG CGGCCCGCGG CCGAGTGGCA CCGCCAGCTG GAGCTGCGCC    540

GCTCGGAGCT GTGACCCCTC CCTCCCCGGT CTCCCTCTGT CTTTGTAATC GGCCTTAGAG    600

ATTAGACATC ATCCTCCACG CCTCTTTGTC CGCCGCCCTT CTTCGCGGAC GGATGAACCA    660

ATTAATTAAT TATTTTTGTC GCTCGCCCGC TCACTCCGGC AAGGGAACGA GTGACGTTAA    720

CTCTCTCACC CTCACGCACA AGAACAAGAA CCGCTCACTC ACCGGGCAAG GGAACACGGT    780

TAAGGTCAAC TCACTCGCGA GAACAAGTTG ACCCTCACTC TAGAGAACGA GGAACGGGCA    840

ACAAGCAACC GTCAACTCAC TTACCACGAG AACAAGTTGA CCGCCACTCA AAGGGAACAG    900

AGAACAGTAA CCGTTCTCGC TCGCTCGGAA CAATAGAACA AGTTAACGTC AACTCGCTCG    960

CTCGGTGTAA GAGAACAACA GAACAAGCAA CTGTTGACCA CTCAACCCCC GGAGAAGAGA   1020

ACAAGAGAGC AGTCAACTCA CCCACTCAGT CTTGGATGAG AGGAGGACGA GTTAACGAGT   1080

ACTCGCACGC AGAGTGAGAG AGTGAGGACA TAATAATAGT TAACGAGTTA ATACTCACTC   1140

GCTCACTCAG AGTGAGAGAG AACCAGTGAG CGAGTTAACC GCGCACACGA GCGAGAGAAC   1200

AGTGAACTGC TCGCGCGCTC GCTCGGTAGC AGTCGGCCTT TCTTAAAACG GTTCGTAAAA   1260

CTTTTCCCGA GACAGTTCAC CCTCCAAAAC TTTTAAAACT AAACTCGGAG GTGGCCTGCC   1320

CTCCACTCTC CGTAAAACTT TTGTAAAACT GTCGGAGGTC GGTCGACTTC GCAACTCGTC   1380

CGCGAAAACT TTTCGTGGGC AGTGTCTGCC TCTCTCAGGC TCCTCGCATC ACTTTCGCGG   1440

AGCCTCGAGG TAGGTCACCT CTCTCCAAAC TTTTGTAAAA ACTTTTTCGC GGAGCCTCTG   1500

GAGGCCGTCC TCCCTCCAAA ACTTTTCGTA AAATCTCTTC GGAGGCCGTC CTCCCTCCAA   1560

AACTTTTCGT AAAATCTTTG GGAGGTCGAC CTCCCTCAAA ACTTTTTATA AAGCTT       1616
```

(2) INFORMATION FOR SEQ ID NO: 5:

(i) SEQUENCE CHARACTERISTICS:
(A) LENGTH: 900 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Parapox ovis
(B) STRAIN: D1701- F9L-Gen (Version 1)

(xi) SEQUENCE DESCRIPTION: SEQ ID NO: 5:

```
GCACCTCGCG CGGCTGGTGC GCCGCGACGT CTTCTCCCGC TGGATAAATG CCGCCGCGGA     60

CGCCCCCGAC GCCGCACTCT CCTGAGCCCA CGCCCGCGGC GCCGGGCTCG CTGTACGACG    120

TCTTCCTCGC GCGCTTCCTG CGCCAGCTGG CCGCGCGCGC GGCGCCGGCC TCGGCCGCCT    180

GCGCCGTGCG CGTGGGTGCG GTGCGCGGCC GCCTGCGGAA CTGCGAGCTG GTGGTGCTGA    240

ACCGCTGCCA CGCGGACGCT GCCGGCGCGC TCGCGCTGGC CTCCGCGGCG CTGGCGGAAA    300

CGCTGGCGGA GCTGCCGCGC GCGGACAGGC TCGCCGTCGC GCGCGAGCTG GGCGTGGACC    360
```

-continued

```
CAGAGCACCC GGAGCTGACG CCGGACCCCG CCTGCGCGGG CGAGAGGCGC GCTTGCGCAG      420

AACATCGACA TCCAGACGCT GGACCTGGGC GACTGCGGCG ACCCCAAAGG CCGCCGACTG      480

CGCGTGGCGC TGGTGAACAG CGGCCACGCG GCCGCAAACT GCGCGCTCGC GCGCGTAGCG      540

ACCGCGCTGA CGCGCCGCGT GCCCGCAAGC CGGCACGGCC TCGCGGAGGG CGGCACGCCG      600

CCGTGGACGC TGCTGCTGGC GGTGGCCGCG GTGACGGTGC TCAGCGTGGT GGCGGTTTCG      660

CTGCTGCGGC GCGCGCTGCG GGTGCGCTAC CAATTCGCGC GGCCGGCCGC GCTGCGCGCG      720

TAGCCGCGCA AAATGTAAAT TATAACGCCC AACTTTTAAG GGTGAGGCGC CATGAAGTTT      780

CTCGTCGGCA TACTGGTAGC TGTGTGCTTG CACCAGTATC TGCTGAACGC GGACAGCACG      840

AAAACATGGT CCGAAGTGTT TGAAAACAGC GGGTGCAAGC CAAGGCCGAT GGTCTTTCGA      900
```

(2) INFORMATION FOR SEQ ID NO: 6:

(i) SEQUENCE CHARACTERISTICS:
        (A) LENGTH: 94 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Parapox ovis
        (B) STRAIN: D1701- VEGF-Promotor (xi) SEQUENCE DESCRIPTION: SEQ ID NO: 6:

```
CCGCGCTGCG CGCGCGTAGC CGCGCAAAAT GTAAATTATA ACGCCCAACT TTTAAGGGTG     60

AGGCGCCATG AAGTTTCTCG TCGGCATACT GGTA                                 94
```

(2) INFORMATION FOR SEQ ID NO: 7:

(i) SEQUENCE CHARACTERISTICS:
(A) LENGTH: 250 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Parapox ovis
(B) STRAIN: D1701- Intergen. Region zwischen HD1R und Proteinkinase Gen (xi) SEQUENCE DESCRIPTION: SEQ ID NO: 7:

```
CAAATGCCGC TTAGTTTCCA GCCTTAAAAG GCAAGTGGGA CCCTGCTCGC TGCCCGGCGA     60

ACTGGTGGAG CGCGTGCTCG CGACCGTGCC ACTGGCCGAC TTGCGCCGCT CGTGCAGCCG    120

CCGCGCGCCC GAGTGACTGC CCATCCCGTT GCTGCGCGAC TCGGGACTGC CCTCTGTTTT    180

TCTTTCCCGT TTCTTCTTAT TAGGTAGTTG TTGCCCACCT CCATGATCCT CGCACGCGCT    240

GGCGGGCGAC                                                           250
```

(2) INFORMATION FOR SEQ ID NO: 8:

(i) SEQUENCE CHARACTERISTICS:

(A) LENGTH: 5515 base pairs
(B) TYPE: nucleic acid
(C) STRANDEDNESS: double
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
(A) ORGANISM: Parapox ovis
(B) STRAIN: D1701- HIND III Fragment I (Version 1)

(xi) SEQUENCE DESCRIPTION: SEQ ID NO: 8:

```
AAGCTTGTTG CGCGAGTACG TGGTGACCCG CGCCTACTCG GATCAGACCG AGCCGATCAT      60
GGACTTGCTC ATCGGCATGG GCGCCGACGT GGACATGCAG GTCGGCGTGT GCCGCACGGC     120
GCTGCACGCC TGCCTTACGG GCTTGAACAC GAACCCGTGC ATGATTCGCG CGCTGCTTCG     180
GCGCGGCGCC AGCGTGACCG CAAAAGACAC CTACGAGATG ACGCCACTGG CGTGTTGCTG     240
AAGTCCGCGA GCGCGACGCC GGAGCTCGTG CGCATCCTCG TGGAAGCAGG CTCCGACGTG     300
AGCGCCACCG ACTTCCGCCT CAACGGCATG CTGCACCAGC ACGCAGTCCA CGCGCCCGCG     360
CGCGAGCGTC ATGCGCGAGC TCATCCGGCT GGGGTGCAGC CCAGCGGCCA AAAACATGTT     420
TGGGAACACG CCGATGCACA TGCTGGCCAT GGAAAGCTCC TGCCGCCGCT CGCTGATCCT     480
CCCGCTGCTG GAGGCAGGGC TTTCCGTGAA CGAGGAGAAC CTGCACTACG GCACCGTGCC     540
TCTGCACGTG GCCTCGGGGT ACGACAACAC GCAGGGCTGC CTCAAGCTCC TCCGGCAGGG     600
AGGAGACCCC ACCGTCGTGT CAGCCGCCGG ACGCACACCG ATCTCGAACA TGCTCGTCAA     660
ACGCAACCAC GTGGCGGTCG CCGGCGCGCT GTCGACGCAC CCGAGCGCGG CAGTGGTCGT     720
GCAGGCTCTC GAGCAGGCTC TCGAGAACGT GCTGAACGCC GGGCCCAGCG AGGCCTCGCG     780
GCTCGCCGTG GCCTTTGTGG TGGCGCGCGC CGGCGCATCC GCGCTACCGG AGGCCGTGCG     840
CCGTCTTCAC GAGGGCTTCG TCGCCGACTG CGAGCGCGAA GTCGCGTTGC TTTCCCGCAG     900
CATGCTCGGC ACACCGGCCG TGAGCGCGCT GGTCGTGCTG GTCAGCAAGG AGGTCTTTGG     960
CACTGTTATC TCCTCGCGTG CGCTGCGCGT CGCGCGGGAG GTCCGCGTGT ACGCAAGGCC    1020
GCTCCGCGAG GCGCTCATAA ATCTGCGCCA CAAATGCCGC TTAGTTTCCA GCCTTAAAAG    1080
GCAAGTGGGA CCCTGCTCGC TGCCCGGCGA ACTGGTGGAG CGCGTGCTCG CGACCGTGCC    1140
ACTGGCCGAC TTGCGCCGCT CGTGCAGCCG CCGCGCGCCC GAGTGACTGC CCATCCCGTT    1200
GCTGCGCGAC TCGGGACTGC CCTCTGTTTT TCTTTCCCGT TTCTTCTTAT TAGGTAGTTG    1260
TTGCCCACCT CCATGATCCT CGCACGCGCT GGCGGGCGAC CTCGCACGCC CGCGGCGGCC    1320
GCGGCGGCCG CCGAGGACGG CAAGAACAGT GATCGCCGGA AGCGCAAGCG CAAGACGCCC    1380
AACTGCGAAG ACGCCGACAA CTCCGACGAC GAGCTAGCGC AGACGCCGTG CGACCGCGAG    1440
TGGCCGGACT GTCGCGCGAG CTCGATCACG AGCTCCGACT CGGTCTCTCT CGGCGACGAG    1500
ATCTACTTGC GGTACGTAGC CTCGCAGGTG GACTTCGCGC AGACCTGGGC CCCGCCGGTG    1560
CGGCTGCTGC GCTTCTTCGG GAACTTCTCG AAGGAAACGC TCAGCCGCAT GTCGCGGCGC    1620
GGGTACGTGA ACCGCTCCTA CTTCCAGATG GCGCACGCGC GCTTCTCGCC CACCAACGAC    1680
GACATGTACC ACATGGCCAC TGGCGGGTAC GGCATCGTGT TCCGCTTCGA CCGCTACGTG    1740
GTCAAGTACG TCTTCGAGCA CCGCAACGGC ATGTCCGAGA TGGACGCCTC TACGGAGTAC    1800
ACGGTGCCGC GGTTCCTGCG CAATAACCTC AAGGGCGACG AGCGCGAGTT CGTGGTCTGC    1860
```

-continued

```
GCGCTGGCCA TGGGGCTGAA CTACCGGCTG GGCTTCCTGC ACTCGCTGTA CCGGCGCGTG    1920

CTGCACACGC TGCTGCTGCT CATGCGCGTG GAGGAAGGCC AGCGGCCCTC GGTAGAGATG    1980

GCCAAGAAGC CGCTGCTGCG CTGGTTCGAG GCGCGCAAGG ACAGCGAGTC CTTCGTGCGC    2040

CTGGTCTCGT ACTTCTACCC CTCGGCCGTG CAGAGCAACG TGAACCTGAT CAACAACTTC    2100

CACCACCTGG TGCACTTCTT TGAGCACGAG AAGCGCGCGC GGTACGTGTT CGACCGCGGG    2160

GCCGTGATCG TGTTCCCTCT GGCGCGCGGG TCCGCGGACT CGATCTCGCC GGAGGCGGCG    2220

GCAGCGCTGG GCTTCGCGCC GCACTCGGAG TTCCTCAAGT TCGTGTTCCT GCAGATCGCG    2280

CTGCTGTACC TGAAGATATA CGAGCTCCCG GGCTGCACGA ACTTCCTGCA CGTGGACCTG    2340

AAGCCCGACA ACGTGCTCAT CTTCGACAGC GCGCGCGCTC AGCGTGACTG CGGCCGGTGC    2400

GACTTTTCGC TTCGAAGAGC CCGTGCGCGC GGCGCTGAAC GACTTCGACT TCGCGCGCGT    2460

GGCCACCATC GAGAACCGCA AGATCGCGGG CAGCGTCCGC GTGCCGCAGA ACTGGTACTA    2520

CGACTTCCAC TTCTTCGCGC ACACGCTGCT GCGCGCGTAC CCGCACATCG CCGCGGAGGA    2580

CCCGGGCTTC CACGCGCTGC TCTCGGAGCT CACGGTCTCG TGCTCGCGCG GGACCTGCGA    2640

CCGCTTCCGG CTGCGCGTGT CCTCGCCGCA CCCCATCGAG CACCTCGCGC GGCTGGTGCG    2700

CCGCGACGTC TTCTCCCGCT GGATAAATGC CGCGCGGAC GCCCCGACG CCGCACTCTC    2760

CTGAGCCCAC GCCCGCGGCG CCGGGCTCGC TGTACGACGT CTTCCTCGCG CGCTTCCTGC    2820

GCCAGCTGGC CGCGCGCGCG GCGCCGGCCT CGGCCGCCTG CGCCGTGCGC GTGGGTGCGG    2880

TGCGCGGCCG CCTGCGGAAC TGCGAGCTGG TGGTGCTGAA CCGCTGCCAC GCGGACGCTG    2940

CCGGCGCGCT CGCGCTGGCC TCCGCGGCGC TGGCGGAAAC GCTGGCGGAG CTGCCGCGCG    3000

CGGACAGGCT CGCCGTCGCG CGCGAGCTGG GCGTGGACCC AGAGCACCCG GAGCTGACGC    3060

CGGACCCCGC CTGCGCGGGC GAGAGGCGCG CTTGCGCAGA ACATCGACAT CCAGACGCTG    3120

GACCTGGGCG ACTGCGGCGA CCCCAAAGGC CGCCGACTGC GCGTGGCGCT GGTGAACAGC    3180

GGCCACGCGG CCGCAAACTG CGCGCTCGCG CGCGTAGCGA CCGCGCTGAC GCGCCGCGTG    3240

CCCGCAAGCC GGCACGGCCT CGCGGAGGGC GGCACGCCGC CGTGGACGCT GCTGCTGGCG    3300

GTGGCCGCGG TGACGGTGCT CAGCGTGGTG GCGGTTTCGC TGCTGCGGCG CGCGCTGCGG    3360

GTGCGCTACC AATTCGCGCG GCCGGCCGCG CTGCGCGCGT AGCCGCGCAA AATGTAAATT    3420

ATAACGCCCA ACTTTTAAGG GTGAGGCGCC ATGAAGTTTC TCGTCGGCAT ACTGGTAGCT    3480

GTGTGCTTGC ACCAGTATCT GCTGAACGCG GACAGCACGA AAACATGGTC CGAAGTGTTT    3540

GAAAACAGCG GGTGCAAGCC AAGGCCGATG GTCTTTCGAG TACACGACGA GCACCCGGAG    3600

CTAACTTCTC AGCGGTTCAA CCCGCCGTGT GTCACGTTGA TGCGATGCGG CGGGTGCTGC    3660

AACGACGAGA GCTTAGAATG CGTCCCCACG GAAGAGGCAA ACGTAACGAT GCAACTCATG    3720

GGAGCGTCGG TCTCCGGTGG TAACGGGATG CAACATCTGA GCTTCGTAGA GCATAAGAAA    3780

TGCGATTGTA AACCACCACT CACGACCACG CCACCGACGA CCACAAGGCC GCCCAGAAGA    3840

CGCCGCTAGA ACTTTTTATG GACCGCATAT CCAAACGATG ATGCGATCAG GTCATGCGGA    3900

AGGAGGCTCC ACGGAGCAAA GTGAAAAAGG ACCGCCTAGA GTCGAGACCC CTCCCTCCCG    3960

CCTCGGGCAA ACCCACAGCC GCCGCAAACA CCACACCCGC CGACCTACCA TGCACCCCTC    4020

GCCGCGCCGG CTGCTCGGCG CGCTCGCGCT GCTGGCGCTG GCTTCGCTC GGCGCGCTCT    4080

TCGCCCCGCG GCGCCGCTCG TGCCGGCCGC CTTCCTGGAG GTGGGGCACG TGCGCGCGAA    4140

CCCGTCCGCC TCGGTGACCT GCCTCACGGT GGGCGGCGAC GGGCGGCACA TGGCGGCGGT    4200

CGCGCACGGC GGCGGGACGC TCTCGCCGGT GTACCCGCTG CCGCCGGCA TGCACGCGAC    4260
```

-continued

```
CTTCTCCTCC GCGCGCAAGG GCGCGCTGCT GCTGAACGTC GCGACCGTGA CTGTGTACGA    4320

CGTGCGCGCG CTCGCCCCCG AGTTCGAGCT CGTCTGCATC GCGGTGGTCG GCGGCTACAA    4380

CTCGGCCGCG GCCGCCACGC GGCCCGCGGC CGAGTGGCAC CGCCAGCTGG AGCTGCGCCG    4440

CTCGGAGCTG TGACCCCTCC CTCCCCGGTC TCCCTCTGTC TTTGTAATCG GCCTTAGAGA    4500

TTAGACATCA TCCTCCACGC CTCTTTGTCC GCCGCCCTTC TTCGCGGACG GATGAACCAA    4560

TTAATTAATT ATTTTTGTCG CTCGCCCGCT CACTCCGGCA AGGGAACGAG TGACGTTAAC    4620

TCTCTCACCC TCACGCACAA GAACAAGAAC CGCTCACTCA CCGGGCAAGG GAACACGGTT    4680

AAGGTCAACT CACTCGCGAG AACAAGTTGA CCCTCACTCT AGAGAACGAG GAACGGGCAA    4740

CAAGCAACCG TCAACTCACT TACCACGAGA ACAAGTTGAC CGCCACTCAA AGGGAACAGA    4800

GAACAGTAAC CGTTCTCGCT CGCTCGGAAC AATAGAACAA GTTAACGTCA ACTCGCTCGC    4860

TCGGTGTAAG AGAACAACAG AACAAGCAAC TGTTGACCAC TCAACCCCCG GAGAAGAGAA    4920

CAAGAGAGCA GTCAACTCAC CCACTCAGTC TTGGATGAGA GGAGGACGAG TTAACGAGTA    4980

CTCGCACGCA GAGTGAGAGA GTGAGGACAT AATAATAGTT AACGAGTTAA TACTCACTCG    5040

CTCACTCAGA GTGAGAGAGA ACCAGTGAGC GAGTTAACCG CGCACACGAG CGAGAGAACA    5100

GTGAACTGCT CGCGCGCTCG CTCGGTAGCA GTCGGCCTTT CTTAAAACGG TTCGTAAAAC    5160

TTTTCCCGAG ACAGTTCACC CTCCAAAACT TTTAAAACTA AACTCGGAGG TGGCCTGCCC    5220

TCCACTCTCC GTAAAACTTT TGTAAAACTG TCGGAGGTCG GTCGACTTCG CAACTCGTCC    5280

GCGAAAACTT TTCGTGGGCA GTGTCTGCCT CTCTCAGGCT CCTCGCATCA CTTTCGCGGA    5340

GCCTCGAGGT AGGTCACCTC TCTCCAAACT TTTGTAAAAA CTTTTTCGCG GAGCCTCTGG    5400

AGGCCGTCCT CCCTCCAAAA CTTTTCGTAA AATCTCTTCG GAGGCCGTCC TCCCTCCAAA    5460

ACTTTTCGTA AAATCTTTGG GAGGTCGACC TCCCTCAAAA CTTTTTATAA AGCTT         5515
```

(2) INFORMATION FOR SEQ ID NO: 9:

(i) SEQUENCE CHARACTERISTICS:
        (A) LENGTH: 1620 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Parapox ovis
        (B) STRAIN: D1701 Proteinkinase-Gen F10L (Version2)

(xi) SEQUENCE DESCRIPTION: SEQ ID NO: 9:

CGAGTGACTG CCCATCCCGT TGCTGCGCGA CTCGGGACTG CCCTCTGTTT TTCTTTCCCG 60

TTTCTTCTTA TTAGGTAGTT GTTGCCCACC TCCATGATCC TCGCACGCGC TGGCGGGCGA 120

CCTCGCACGC CCGCGGCGGC CGCGGCGGCC GCCGAGGACG GCAAGAACAG TGATCGCCGG 180

AAGCGCAAGC GCAAGACGCC CAACTGCGAA GACGCCGACA ACTCCGACGA CGAGCTAGCG 240

CAGACGCCGT GCGACCGCGA GTGGCCGGAC TGTCGCGCGA GCTCGATCAC GAGCTCCGAC 300

TCGGTCTCTC TCGGCGACGA GATCTACTTG CGGTACGTAG CCTCGCAGGT GGACTTCGCG 360

CAGACCTGGG CCCCGCCGGT GCGGCTGCTG CGCTTCTTCG GGAACTTCTC GAAGGAAACG 420

CTCAGCCGCA TGTCGCGGCG CGGGTACGTG AACCGCTCCT ACTTCCAGAT GGCGCACGCG 480

-continued

```
CGCTTCTCGC CCACCAACGA CGACATGTAC CACATGGCCA CTGGCGGGTA CGGCATCGTG      540

TTCCGCTTCG ACCGCTACGT GGTCAAGTAC GTCTTCGAGC ACCGCAACGG CATGTCCGAG      600

ATGGACGCCT CTACGGAGTA CACGGTGCCG CGGTTCCTGC GCAATAACCT CAAGGGCGAC      660

GAGCGCGAGT TCGTGGTCTG CGCGCTGGCC ATGGGGCTGA ACTACCGGCT GGGCTTCCTG      720

CACTCGCTGT ACCGGCGCGT GCTGCACACG CTGCTGCTGC TCATGCGCGT GGAGGAAGGC      780

CAGCGGCCCT CGGTAGAGAT GGCCAAGAAG CCGCTGCTGC GCTGGTTCGA GGCGCGCAAG      840

GACAGCGAGT CCTTCGTGCG CCTGGTCTCG TACTTCTACC CCTCGGCCGT GCAGAGCAAC      900

GTGAACCTGA TCAACAACTT CCACCACCTG GTGCACTTCT TGAGCACGA GAAGCGCGCG       960

CGGTACGTGT TCGACCGCGG GGCCGTGATC GTGTTCCCTC TGGCGCGCGG GTCCGCGGAC     1020

TCGATCTCGC CGGAGGCGGC GGCAGCGCTG GGCTTCGCGC GGCACTCGGA GTTCCTCAAG     1080

TTCGTGTTCC TGCAGATCGC GCTGCTGTAC CTGAAGATAT ACGAGCTCCC GGGCTGCACG     1140

AACTTCCTGC ACGTGGACCT GAAGCCCGAC AACGTGCTCA TCTTCGACAG CGCGCGCGCG     1200

CTCAGCGTGA CTGCGGCCGG TGCGACTTTT CGCTTCGAAG AGCCCGTGCG CGCGGCGCTG     1260

AACGACTTCG ACTTCGCGCG CGTGGCCACC ATCGAGAACC GCAAGATCGC GGGCAGCGTC     1320

CGCGTGCCGC AGAACTGGTA CTACGACTTC CACTTCTTCG CGCACACGCT GCTGCGCGCG     1380

TACCCGCACA TCGCCGCGGA GGACCCGGGC TTCCACGCGC TGCTCTCGGA GCTCACGGTC     1440

TCGTGCTCGC GCGGGACCTG CGACCGCTTC CGGCTGCGCG TGTCCTCGCC GCACCCCATC     1500

GAGCACCTCG CGCGGCTGGT GCGCCGCGAC GTCTTCTCCC GCTGGATAAA TGCCGCCGCG     1560

GACGCCCCCG ACGCCGCACT CTCCTGAGCC CACGCCCGCG GCGCCGGGCT CGCTGTACGA     1620
```

(2) INFORMATION FOR SEQ ID NO: 10:

(i) SEQUENCE CHARACTERISTICS:
        (A) LENGTH: 780 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Parapox ovis
        (B) STRAIN: D1701-F9L Gen, Version 2

(xi) SEQUENCE DESCRIPTION: SEQ ID NO: 10:

```
GAGCACCTCG CGCGGCTGGT GCGCCGCGAC GTCTTCTCCC GCTGGATAAA TGCCGCCGCG       60

GACGCCCCCG ACGCCGCACT CTCCTGAGCC CACGCCCGCG GCGCCGGGCT CGCTGTACGA      120

CGTCTTCCTC GCGCGCTTCC TGCGCCAGCT GGCCGCGCGC GCGGCGCCGG CCTCGGCCGC      180

CTGCGCCGTG CGCGTGGGTG CGGTGCGCGG CCGCCTGCGG AACTGCGAGC TGGTGGTGCT      240

GAACCGCTGC CACGCGGACG CTGCCGGCGC GCTCGCGCTG GCCTCCGCGG CGCTGGCGGA      300

AACGCTGGCG GAGCTGCCGC GCGCGGACAG GCTCGCCGTC GCGCGCGAGC TGGGCGTGGA      360

CCCAGAGCAC CCGGAGCTGA CGCCGGACCC CGCCTGCGCG GGCGAGAGCG CGCTTGCGCA      420

GAACATCGAC ATCCAGACGC TGGACCTGGG CGACTGCGGC GACCCCAAAG GCCGCCGACT      480

GCGCGTGGCG CTGGTGAACA GCGGCCACGC GGCCGCAAAC TGCGCGCTCG CGCGCGTAGC      540

GACCGCGCTG ACGCGCCGCG TGCCCGCAAG CCGGCACGGC CTCGCGGAGG GCGGCACGCC      600
```

```
GCCGTGGACG CTGCTGCTGG CGGTGGCCGC GGTGACGGTG CTCAGCGTGG TGGCGGTTTC      660

GCTGCTGCGG CGCGCGCTGC GGGTGCGCTA CCAATTCGCG CGGCCGGCCG CGCTGCGCGC      720

GTAGCCGCGC AAAATGTAAA TTATAACGCC CAACTTTTAA GGGTGAGGCG CCATGAAGTT      780

(2) INFORMATION FOR SEQ ID NO: 11:

(i) SEQUENCE CHARACTERISTICS:
        (A) LENGTH: 297 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Parapox ovis
         (B) STRAIN: D1701 10kD- Gen (xi) SEQUENCE DESCRIPTION: SEQ ID NO: 11:

CAATATGGAG GAAAATGACG GAGAAAACCT ATTGGCTCAG CCTGATGATG ATACAGACAA       60

TTTAACCAAC GGAGTGTACG CGGCTGGAGC TCCAACTAAA GAAAGTGTGG AAGAGCGTCT      120

CGTAAGCTTG TTAGACGGTT ACAAAAATAT AACTGATTGC TGCAGAGAAA CAGGTAACCG      180

GTTAGACAGA CTAGAAAGAC ACTTGGAGAG TCTACGTAAA GCTCTTCTTG ATCTCAACAG      240

AAAAATAGAT GTACAGACAG GATACAGCAG ATATTAGATA CCGCTGTGTT GCGTCTG        297

(2) INFORMATION FOR SEQ ID NO: 12:

(i) SEQUENCE CHARACTERISTICS:
        (A) LENGTH: 5519 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Parapox ovis
         (B) STRAIN: D 1701, HindIII-Fragment I, Version 2

(xi) SEQUENCE DESCRIPTION: SEQ ID NO: 12:

AAGCTTGTTG CGCGAGTACG TGGTGACCCG CGCCTACTCG GATCAGACCG AGCCGATCAT       60

GGACTTGCTC ATCGGCATGG GCGCCGACGT GGACATGCAG GTCGGCGTGT GCCGCACGGC      120

GCTGCACGCC TGCCTTACGG GCTTGAACAC GAACCCGTGC ATGATTCGCG CGCTGCTTCG      180

GCGCGGCGCC AGCGTGACCG CAAAAGACAC CTACGAGATG ACGCCACTGG CGGTGTTGCT      240

GAAGTCCGCG AGCGCGACGC CGGAGCTCGT GCGCATCCTC GTGGAAGCAG GCTCCGACGT      300

GAGCGCCACC GACTTCCGCC TCAACGGCAT GCTGCACCAG CACGCGCAGT CCACGCGCCC      360

GCGCGCGAGC GTCATGCGCG AGCTCATCCG GCTGGGGTGC AGCCCAGCGG CCAAAAACAT      420

GTTTGGGAAC ACGCCGATGC ACATGCTGGC CATGGAAAGC TCCTGCCGCC GCTCGCTGAT      480

CCTCCCGCTG CTGGAGGCAG GGCTTTCCGT GAACGAGGAG AACCTGCACT ACGGCACCGT      540

GCCTCTGCAC GTGGCCTCGG GGTACGACAA CACGCAGGGC TGCCTCAAGC TCCTCCGGCA      600
```

-continued

```
GGGAGGAGAC CCCACCGTCG TGTCAGCCGC CGGACGCACA CCGATCTCGA ACATGCTCGT    660

CAAACGCAAC CACGTGGCGG TCGCCGGCGC GCTGTCGACG CACCCGAGCG CGGCAGTGGT    720

CGTGCAGGCT CTCGAGCAGG CTCTCGAGAA CGTGCTGAAC GCCGGGCCCA GCGAGGCCTC    780

GCGGCTCGCC GTGGCCTTTG TGGTGGCGCG CGCCGGCGCA TCCGCGCTAC CGGAGGCCGT    840

GCGCCGTCTT CACGAGGGCT TCGTCGCCGA CTGCGAGCGC GAAGTCGCGT TGCTTTCCCG    900

CAGCATGCTC GGCACACCGG CCGTGAGCGC GCTGGTCGTG CTGGTCAGCA AGGAGGTCTT    960

TGGCACTGTT ATCTCCTCGC GTGCGCTGCG CGTCGCGCGG GAGGTCCGCG TGTACGCAAG   1020

GCCGCTCCGC GAGGCGCTCA TAAATCTGCG CCACAAATGC CGCTTAGTTT CCAGCCTTAA   1080

AAGGCAAGTG GGACCCTGCT CGCTGCCCGG CGAACTGGTG GAGCGCGTGC TCGCGACCGT   1140

GCCACTGGCC GACTTGCGCC GCTCGTGCAG CCGCCGCGCG CCCGAGTGAC TGCCCATCCC   1200

GTTGCTGCGC GACTCGGGAC TGCCCTCTGT TTTTCTTTCC CGTTTCTTCT TATTAGGTAG   1260

TTGTTGCCCA CCTCCATGAT CCTCGCACGC GCTGGCGGGC GACCTCGCAC GCCCGCGGCG   1320

GCCGCGGCGG CCGCCGAGGA CGGCAAGAAC AGTGATCGCC GGAAGCGCAA GCGCAAGACG   1380

CCCAACTGCG AAGACGCCGA CAACTCCGAC GACGAGCTAG CGCAGACGCC GTGCGACCGC   1440

GAGTGGCCGG ACTGTCGCGC GAGCTCGATC ACGAGCTCCG ACTCGGTCTC TCTCGGCGAC   1500

GAGATCTACT TGCGGTACGT AGCCTCGCAG GTGGACTTCG CGCAGACCTG GCCCCGCCG    1560

GTGCGGCTGC TGCGCTTCTT CGGGAACTTC TCGAAGGAAA CGCTCAGCCG CATGTCGCGG   1620

CGCGGGTACG TGAACCGCTC CTACTTCCAG ATGGCGCACG CGCGCTTCTC GCCCACCAAC   1680

GACGACATGT ACCACATGGC CACTGGCGGG TACGGCATCG TGTTCCGCTT CGACCGCTAC   1740

GTGGTCAAGT ACGTCTTCGA GCACCGCAAC GGCATGTCCG AGATGGACGC CTCTACGGAG   1800

TACACGGTGC CGCGGTTCCT GCGCAATAAC CTCAAGGGCG ACGAGCGCGA GTTCGTGGTC   1860

TGCGCGCTGG CCATGGGGCT GAACTACCGG CTGGGCTTCC TGCACTCGCT GTACCGGCGC   1920

GTGCTGCACA CGCTGCTGCT GCTCATGCGC GTGGAGGAAG GCCAGCGGCC CTCGGTAGAG   1980

ATGGCCAAGA AGCCGCTGCT GCGCTGGTTC GAGGCGCGCA AGGACAGCGA GTCCTTCGTG   2040

CGCCTGGTCT CGTACTTCTA CCCCTCGGCC GTGCAGAGCA ACGTGAACCT GATCAACAAC   2100

TTCCACCACC TGGTGCACTT CTTTGAGCAC GAGAAGCGCG CGCGGTACGT GTTCGACCGC   2160

GGGGCCGTGA TCGTGTTCCC TCTGGCGCGC GGGTCCGCGG ACTCGATCTC GCCGGAGGCG   2220

GCGGCAGCGC TGGGCTTCGC GCCGCACTCG GAGTTCCTCA AGTTCGTGTT CCTGCAGATC   2280

GCGCTGCTGT ACCTGAAGAT ATACGAGCTC CCGGGCTGCA CGAACTTCCT GCACGTGGAC   2340

CTGAAGCCCG ACAACGTGCT CATCTTCGAC AGCGCGCGCG CGCTCAGCGT GACTGCGGCC   2400

GGTGCGACTT TTCGCTTCGA AGAGCCCGTG CGCGCGGCGC TGAACGACTT CGACTTCGCG   2460

CGCGTGGCCA CCATCGAGAA CCGCAAGATC GCGGGCAGCG TCCGCGTGCC GCAGAACTGG   2520

TACTACGACT TCCACTTCTT CGCGCACACG CTGCTGCGCG CGTACCCGCA CATCGCCGCG   2580

GAGGACCCGG GCTTCCACGC GCTGCTCTCG GAGCTCACGG TCTCGTGCTC GCGCGGGACC   2640

TGCGACCGCT TCCGGCTGCG CGTGTCCTCG CCGCACCCCA TCGAGCACCT CGCGCGGCTG   2700

GTGCGCCGCG ACGTCTTCTC CCGCTGGATA AATGCCGCCG CGGACGCCCC CGACGCCGCA   2760

CTCTCCTGAG CCCACGCCCG CGGCGCCGGG CTCGCTGTAC GACGTCTTCC TCGCGCGCTT   2820

CCTGCGCCAG CTGGCCGCGC GCGCGGCGCC GGCCTCGGCC GCCTGCGCCG TGCGCGTGGG   2880

TGCGGTGCGC GGCCGCCTGC GGAACTGCGA GCTGGTGGTG CTGAACCGCT GCCACGCGGA   2940

CGCTGCCGGC GCGCTCGCGC TGGCCTCCGC GGCGCTGGCG GAAACGCTGG CGGAGCTGCC   3000
```

```
GCGCGCGGAC AGGCTCGCCG TCGCGCGCGA GCTGGGCGTG GACCCAGAGC ACCCGGAGCT   3060

GACGCCGGAC CCCGCCTGCG CGGGCGAGAG CGCGCTTGCG CAGAACATCG ACATCCAGAC   3120

GCTGGACCTG GGCGACTGCG GCGACCCCAA AGGCCGCCGA CTGCGCGTGG CGCTGGTGAA   3180

CAGCGGCCAC GCGGCCGCAA ACTGCGCGCT CGCGCGCGTA GCGACCGCGC TGACGCGCCG   3240

CGTGCCCGCA AGCGGCACG GCCTCGCGGA GGGCGGCACG CCGCCGTGGA CGCTGCTGCT   3300

GGCGGTGGCC GCGGTGACGG TGCTCAGCGT GGTGGCGGTT TCGCTGCTGC GGCGCGCGCT   3360

GCGGGTGCGC TACCAATTCG CGCGGCCGGC CGCGCTGCGC GCGTAGCCGC GCAAAATGTA   3420

AATTATAACG CCCAACTTTT AAGGGTGAGG CGCCATGAAG TTTCTCGTCG GCATACTGGT   3480

AGCTGTGTGC TTGCACCAGT ATCTGCTGAA CGCGGACAGC ACGAAAACAT GGTCCGAAGT   3540

GTTTGAAAAC AGCGGGTGCA AGCCAAGGCC GATGGTCTTT CGAGTACACG ACGAGCACCC   3600

GGAGCTAACT TCTCAGCGGT TCAACCCGCC GTGTGTCACG TTGATGCGAT GCGGCGGGTG   3660

CTGCAACGAC GAGAGCTTAG AATGCGTCCC CACGGAAGAG GCAAACGTAA CGATGCAACT   3720

CATGGGAGCG TCGGTCTCCG GTGGTAACGG GATGCAACAT CTGAGCTTCG TAGAGCATAA   3780

GAAATGCGAT TGTAAACCAC CACTCACGAC CACGCCACCG ACGACCACAA GGCCGCCCAG   3840

AAGACGCCGC TAGAACTTTT TATGGACCGC ATATCCAAAC GATGATGCGA TCAGGTCATG   3900

CGGAAGGAGG CTCCACGGAG CAAAGTGAAA AAGGACCGCC TAGAGTCGAG ACCCCTCCCT   3960

CCCGCCTCGG GCAAACCCAC AGCCGCCGCA AACACCACAC CCGCCGACCT ACCATGCACC   4020

CCTCGCCGCG CCGGCTGCTC GGCGCGCTCG CGCTGCTGGC GCTGGGCTTC GCTCGGCGCG   4080

CTCTTCGCCC CGCGGCGCCG CTCGTGCCGG CCGCCTTCCT GGAGGTGGGG CACGTGCGCG   4140

CGAACCCGTC CGCCTCGGTG ACCTGCCTCA CGGTGGGCGG CGACGGGCGG CACATGGCGG   4200

CGGTCGCGCA CGGCGGCGGG ACGCTCTCGC CGGTGTACCC GCTGGCCGCC GGCATGCACG   4260

CGACCTTCTC CTCCGCGCGC AAGGGCGCGC TGCTGCTGAA CGTCGCGACC GTGACTGTGT   4320

ACGACGTGCG CGCGCTCGCC CCCGAGTTCG AGCTCGTCTG CATCGCGGTG GTCGGCGGCT   4380

ACAACTCGGC CGCGGCCGCC ACGCGGCCCG CGGCCGAGTG GCACCGCCAG CTGGAGCTGC   4440

GCCGCTCGGA GCTGTGACCC CTCCCTCCCC GGTCTCCCTC TGTCTTTGTA ATCGGCCTTA   4500

GAGATTAGAC ATCATCCTCC ACGCCTCTTT GTCCGCCGCC CTTCTTCGCG GACGGATGAA   4560

CCAATTAATT AATTATTTTT GTCGCTCGCC CGCTCACTCC GGCAAGGGAA CGAGTGACGT   4620

TAACTCTCTC ACCCTCACGC ACAAGAACAA GAACCGCTCA CTCACCGGGC AAGGGAACAC   4680

GGTTAAGGTC AACTCACTCG CGAGAACAAG TTGACCCTCA CTCTAGAGAA CGAGGAACGG   4740

GCAACAAGCA ACCGTCAACT CACTTACCAC GAGAACAAGT TGACCGCCAC TCAAAGGGAA   4800

CAGAGAACAG TAACCGTTCT CGCTCGCTCG GAACAATAGA ACAAGTTAAC GTCAACTCGC   4860

TCGCTCGGTG TAAGAGAACA ACAGAACAAG CAACTGTTGA CCACTCAACC CCCGGAGAAG   4920

AGAACAAGAG AGCAGTCAAC TCACCCACTC AGTCTTGGAT GAGAGGAGGA CGAGTTAACG   4980

AGTACTCGCA CGCAGAGTGA GAGAGTGAGG ACATAATAAT AGTTAACGAG TTAATACTCA   5040

CTCGCTCACT CAGAGTGAGA GAGAACCAGT GAGCGAGTTA ACCGCGCACA CGAGCGAGAG   5100

AACAGTGAAC TGCTCGCGCG CTCGCTCGGT AGCAGTCGGC CTTTCTTAAA ACGGTTCGTA   5160

AAACTTTTCC CGAGACAGTT CACCCTCCAA AACTTTTAAA ACTAAACTCG GAGGTGGCCT   5220

GCCCTCCACT CTCCGTAAAA CTTTTGTAAA ACTGTCGGAG GTCGGTCGAC TTCGCAACTC   5280

GTCCGCGAAA ACTTTTCGTG GGCAGTGTCT GCCTCTCTCA GGCTCCTCGC ATCACTTTCG   5340
```

-continued

```
CGGAGCCTCG AGGTAGGTCA CCTCTCTCCA AACTTTTGTA AAAACTTTTT CGCGGAGCCT    5400

CTGGAGGCCG TCCTCCCTCC AAAACTTTTC GTAAAATCTC TTCGGAGGCC GTCCTCCCTC    5460

CAAAACTTTT CGTAAAATCT TTGGGAGGTC GACCTCCCTC AAAACTTTTT ATAAAGCTT     5519
```

(2) INFORMATION FOR SEQ ID NO: 13:

(i) SEQUENCE CHARACTERISTICS:
        (A) LENGTH: 1742 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Parapox ovis
        (B) STRAIN: D 1701 Proteinkinase-Gen F10L ( Version 3)

(xi) SEQUENCE DESCRIPTION: SEQ ID NO: 13:

```
CGAGTGACTG CCCATCCCGT TGCTGCGCGA CTCGGGACTG CCCTCTGTTT TTCTTTCCCG      60

TTTCTTCTTA TTAGGTAGTT GTTGCCCACC TCCATGATCC TCGCACGCGC TGGCGGGCGA     120

CCTCGCACGC CCGCGGCGGC CGCGGCGGCC GCCGAGGACG GCAAGAACAG TGATCGCCGG     180

AAGCGCAAGC GCAAGACGCC CAACTGCGAA GACGCCGACA ACTCCGACGA CGAGCTAGCG     240

CAGACGCCGT GCGACCGCGA GTGGCCGGAC TGTCGCGCGA GCTCGATCAC GAGCTCCGAC     300

TCGGTCTCTC TCGGCGACGA GATCTACTTG CGGTACGTAG CCTCGCAGGT GGACTTCGCG     360

CAGACCTGGG CCCCGCCGGT GCGGCTGCTG CGCTTCTTCG GGAACTTCTC GAAGGAAACG     420

CTCAGCCGCA TGTCGCGGCG CGGGTACGTG AACCGCTCCT ACTTCCAGAT GGCGCACGCG     480

CGCTTCTCGC CCACCAACGA CGACATGTAC CACATGGCCA CTGGCGGGTA CGGCATCGTG     540

TTCCGCTTCG ACCGCTACGT GGTCAAGTAC GTCTTCGAGC ACCGCAACGG CATGTCCGAG     600

ATGGACGCCT CTACGGAGTA CACGGTGCCG CGGTTCCTGC GCAATAACCT CAAGGGCGAC     660

GAGCGCGAGT TCGTGGTCTG CGCGCTGGCC ATGGGGCTGA ACTACCGGCT GGGCTTCCTG     720

CACTCGCTGT ACCGGCGCGT GCTGCACACG CTGCTGCTGC TCATGCGCGT GGAGGAAGGC     780

CAGCGGCCCT CGGTAGAGAT GGCCAAGAAG CCGCTGCTGC GCTGGTTCGA GGCGCGCAAG     840

GACAGCGAGT CCTTCGTGCG CCTGGTCTCG TACTTCTACC CCTCGGCCGT GCAGAGCAAC     900

GTGAACCTGA TCAACAACTT CCACCACCTG GTGCACTTCT TGAGCACGA GAAGCGCGCG     960

CGGTACGTGT TCGACCGCGG GGCCGTGATC GTGTTCCCTC TGGCGCGCGG GTCCGCGGAC    1020

TCGATCTCGC CGGAGGCGGC GGCAGCGCTG GGCTTCGCGC CGCACTCGGA GTTCCTCAAG    1080

TTCGTGTTCC TGCAGATCGC GCTGCTGTAC CTGAAGATAT ACGAGCTCCC GGGCTGCACG    1140

AACTTCCTGC ACGTGGACCT GAAGCCCGAC AACGTGCTCA TCTTCGACAG CGCGCGCGCG    1200

CTCAGCGTGA CTGCGGCCGG TGCGACTTTT CGCTTCGAAG AGCCCGTGCG CGCGGCGCTG    1260

AACGACTTCG ACTTCGCGCG CGTGGCCACC ATCGAGAACC GCAAGATCGC GGGCAGCGTC    1320

CGCGTGCCGC AGAACTGGTA CTACGACTTC CACTTCTTCG CGCACACGCT GCTGCGCGCG    1380

TACCCGCACA TCGCCGCGGA GGACCCGGGC TTCCACGCGC TGCTCTCGGA GCTCACGGTC    1440

TCGTGCTCGC GCGGGACCTG CGACCGCTTC CGGCTGCGCG TGTCCTCGCC GCACCCCATC    1500

GAGCACCTCG CGCGGCTGGT GCGCCGCGAC GTCTTCCTCCC GCTGGATAAA TGCCGCCGCG    1560
```

```
GACGCCCCCG ACGCCGCACT CTCCTGAGCC CACGCCCGCG GCGCCGGGCT CGCTGTACGA    1620

CGTCTTCCTC GCGCGCTTCC TGCGCCAGCT GGCCGCGCGC GCGGCGCCGG CCTCGGCCGC    1680

CTGCGCCGTG CGCGTGGGTG CGGTGCGCGG CCGCCTGCGG AACTGCGAGC TGGTGGTGCT    1740

GA                                                                  1742
```

(2) INFORMATION FOR SEQ ID NO: 14:

(i) SEQUENCE CHARACTERISTICS:
        (A) LENGTH: 497 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Parapox ovis
        (B) STRAIN: D1701 Proteinkinase F10L (xi) SEQUENCE DESCRIPTION: SEQ ID NO: 14:

```
Met Ile Leu Ala Arg Ala Gly Gly Arg Pro Arg Thr Pro Ala Ala Ala
 1               5                  10                  15

Ala Ala Ala Ala Glu Asp Gly Lys Asn Ser Asp Arg Arg Lys Arg Lys
            20                  25                  30

Arg Lys Thr Pro Asn Cys Glu Asp Ala Asp Asn Ser Asp Asp Glu Leu
        35                  40                  45

Ala Gln Thr Pro Cys Asp Arg Glu Trp Pro Asp Cys Arg Ala Ser Ser
    50                  55                  60

Ile Thr Ser Ser Asp Ser Val Ser Leu Gly Asp Glu Ile Tyr Leu Arg
65                  70                  75                  80

Tyr Val Ala Ser Gln Val Asp Phe Ala Gln Thr Trp Ala Pro Pro Val
                85                  90                  95

Arg Leu Leu Arg Phe Phe Gly Asn Phe Ser Lys Glu Thr Leu Ser Arg
            100                 105                 110

Met Ser Arg Arg Gly Tyr Val Asn Arg Ser Tyr Phe Gln Met Ala His
        115                 120                 125

Ala Arg Phe Ser Pro Thr Asn Asp Asp Met Tyr His Met Ala Thr Gly
    130                 135                 140

Gly Tyr Gly Ile Val Phe Arg Phe Asp Arg Tyr Val Val Lys Tyr Val
145                 150                 155                 160

Phe Glu His Arg Asn Gly Met Ser Glu Met Asp Ala Ser Thr Glu Tyr
                165                 170                 175

Thr Val Pro Arg Phe Leu Arg Asn Asn Leu Lys Gly Asp Glu Arg Glu
            180                 185                 190

Phe Val Val Cys Ala Leu Ala Met Gly Leu Asn Tyr Arg Leu Gly Phe
        195                 200                 205

Leu His Ser Leu Tyr Arg Arg Val Leu His Thr Leu Leu Leu Leu Met
    210                 215                 220

Arg Val Glu Glu Gly Gln Arg Pro Ser Val Glu Met Ala Lys Lys Pro
225                 230                 235                 240

Leu Leu Arg Trp Phe Glu Ala Arg Lys Asp Ser Glu Ser Phe Val Arg
                245                 250                 255

Leu Val Ser Tyr Phe Tyr Pro Ser Ala Val Gln Ser Asn Val Asn Leu
            260                 265                 270
```

-continued

Ile Asn Asn Phe His His Leu Val His Phe Phe Glu His Glu Lys Arg
275 280 285

Ala Arg Tyr Val Phe Asp Arg Gly Ala Val Ile Val Phe Pro Leu Ala
290 295 300

Arg Gly Ser Ala Asp Ser Ile Ser Pro Glu Ala Ala Ala Ala Leu Gly
305 310 315 320

Phe Ala Pro His Ser Glu Phe Leu Lys Phe Val Phe Leu Gln Ile Ala
325 330 335

Leu Leu Tyr Leu Lys Ile Tyr Glu Leu Pro Gly Cys Thr Asn Phe Leu
340 345 350

His Val Asp Leu Lys Pro Asp Asn Val Leu Ile Phe Asp Ser Ala Arg
355 360 365

Ala Leu Ser Val Thr Ala Ala Gly Ala Thr Phe Arg Phe Glu Glu Pro
370 375 380

Val Arg Ala Ala Leu Asn Asp Phe Asp Phe Ala Arg Val Ala Thr Ile
385 390 395 400

Glu Asn Arg Lys Ile Ala Gly Ser Val Arg Val Pro Gln Asn Trp Tyr
405 410 415

Tyr Asp Phe His Phe Phe Ala His Thr Leu Leu Arg Ala Tyr Pro His
420 425 430

Ile Ala Ala Glu Asp Pro Gly Phe His Ala Leu Leu Ser Glu Leu Thr
435 440 445

Val Ser Cys Ser Arg Gly Thr Cys Asp Arg Phe Arg Leu Arg Val Ser
450 455 460

Ser Pro His Pro Ile Glu His Leu Ala Arg Leu Val Arg Arg Asp Val
465 470 475 480

Phe Ser Arg Trp Ile Asn Ala Ala Ala Asp Ala Pro Asp Ala Ala Leu
485 490 495

Ser (2) INFORMATION FOR SEQ ID NO: 15:

(i) SEQUENCE CHARACTERISTICS:
(A) LENGTH: 132 amino acids
(B) TYPE: amino acid
(C) STRANDEDNESS: single
(D) TOPOLOGY: linear (ii) MOLECULE TYPE: protein (iii) HYPOTHETICAL: NO (iv) ANTI-SENSE: NO (vi) ORIGINAL SOURCE:
(A) ORGANISM: Parapox ovis
(B) STRAIN: D1701 VEGF- Protein (xi) SEQUENCE DESCRIPTION: SEQ ID NO: 15:

Met Lys Phe Leu Val Gly Ile Leu Val Ala Val Cys Leu His Gln Tyr
1 5 10 15

Leu Leu Asn Ala Asp Ser Thr Lys Thr Trp Ser Glu Val Phe Glu Asn
20 25 30

Ser Gly Cys Lys Pro Arg Pro Met Val Phe Arg Val His Asp Glu His
35 40 45

Pro Glu Leu Thr Ser Gln Arg Phe Asn Pro Pro Cys Val Thr Leu Met
50 55 60

Arg Cys Gly Gly Cys Cys Asn Asp Glu Ser Leu Glu Cys Val Pro Thr

```
            65                  70                  75                  80
Glu Glu Ala Asn Val Thr Met Gln Leu Met Gly Ala Ser Val Ser Gly
                    85                  90                  95

Gly Asn Gly Met Gln His Leu Ser Phe Val Glu His Lys Lys Cys Asp
                100                 105                 110

Cys Lys Pro Pro Leu Thr Thr Thr Pro Pro Thr Thr Thr Arg Pro Pro
            115                 120                 125

Arg Arg Arg Arg
        130
```

(2) INFORMATION FOR SEQ ID NO: 16:

(i) SEQUENCE CHARACTERISTICS:
        (A) LENGTH: 224 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Parapox ovis
        (B) STRAIN: D1701 Protein F9L (xi) SEQUENCE DESCRIPTION: SEQ ID NO: 16:

```
Met Pro Pro Arg Thr Pro Pro Thr Pro His Ser Pro Glu Pro Thr Pro
1               5                   10                  15

Ala Ala Pro Gly Ser Leu Tyr Asp Val Phe Leu Ala Arg Phe Leu Arg
                20                  25                  30

Gln Leu Ala Ala Arg Ala Ala Pro Ala Ser Ala Ala Cys Ala Val Arg
            35                  40                  45

Val Gly Ala Val Arg Gly Arg Leu Arg Asn Cys Glu Leu Val Val Leu
50                  55                  60

Asn Arg Cys His Ala Asp Ala Ala Gly Ala Leu Ala Leu Ala Ser Ala
65                  70                  75                  80

Ala Leu Ala Glu Thr Leu Ala Glu Leu Pro Arg Ala Asp Arg Leu Ala
                85                  90                  95

Val Ala Arg Glu Leu Gly Val Asp Pro Glu His Pro Glu Leu Thr Pro
                100                 105                 110

Asp Pro Ala Cys Ala Gly Glu Ser Ala Leu Ala Gln Asn Ile Asp Ile
            115                 120                 125

Gln Thr Leu Asp Leu Gly Asp Cys Gly Asp Pro Lys Gly Arg Arg Leu
            130                 135                 140

Arg Val Ala Leu Val Asn Ser Gly His Ala Ala Ala Asn Cys Ala Leu
145                 150                 155                 160

Ala Arg Val Ala Thr Ala Leu Thr Arg Val Pro Ala Ser Arg His
                165                 170                 175

Gly Leu Ala Glu Gly Gly Thr Pro Pro Trp Thr Leu Leu Leu Ala Val
                180                 185                 190

Ala Ala Val Thr Val Leu Ser Val Val Ala Val Ser Leu Leu Arg Arg
            195                 200                 205

Ala Leu Arg Val Arg Tyr Gln Phe Ala Arg Pro Ala Ala Leu Arg Ala
            210                 215                 220
```

(2) INFORMATION FOR SEQ ID NO: 17:

-continued

```
     (i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: no (iv) ANTI-SENSE: no (vi) ORIGINAL SOURCE:
          (A) ORGANISM: Parapox ovis
          (B) STRAIN: NZ-2

(xi) SEQUENCE DESCRIPTION: SEQ ID NO: 17:

CAATATGGAT GAAAATGACG G                                                      21

(2) INFORMATION FOR SEQ ID NO: 18:

(i) SEQUENCE CHARACTERISTICS:
          (A) LENGTH: 17 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: no (iv) ANTI-SENSE: no (vi) ORIGINAL SOURCE:
          (A) ORGANISM: Parapox ovis
          (B) STRAIN: NZ-2

(xi) SEQUENCE DESCRIPTION: SEQ ID NO: 18:

CAGACGGCAA CACAGCG                                                           17
```